United States Patent
Atsushi et al.

(10) Patent No.: US 7,169,892 B2
(45) Date of Patent: Jan. 30, 2007

(54) LIPID-PEPTIDE-POLYMER CONJUGATES FOR LONG BLOOD CIRCULATION AND TUMOR SPECIFIC DRUG DELIVERY SYSTEMS

(75) Inventors: Maeda Atsushi, Shizuoka (JP); Akira Takagi, Shizuoka (JP); Katsumi Saito, Shizuoka (JP); Noboru Yamashita, Shizuoka (JP); Tatsnobu Yoshioka, Shizuoka (JP)

(73) Assignee: Astellas Pharma Inc., Tokyo (JP)

( * ) Notice: Subject to any disclaimer, the term of this patent is extended or adjusted under 35 U.S.C. 154(b) by 101 days.

(21) Appl. No.: 10/754,341

(22) Filed: Jan. 9, 2004

(65) Prior Publication Data

US 2005/0054026 A1    Mar. 10, 2005

Related U.S. Application Data

(60) Provisional application No. 60/439,560, filed on Jan. 10, 2003.

(51) Int. Cl.
*A61K 38/08*     (2006.01)
*C07K 7/00*      (2006.01)
*C07K 17/00*     (2006.01)

(52) U.S. Cl. .............. 530/328; 530/345; 530/300; 435/212; 435/176; 435/177

(58) Field of Classification Search ............ None
See application file for complete search history.

(56) References Cited

U.S. PATENT DOCUMENTS 6,339,069 B1 * 1/2002 Meers et al. ............ 514/44

FOREIGN PATENT DOCUMENTS

| WO | WO 91/05546 | 5/1991 |
| WO | WO 98/16240 | 4/1998 |
| WO | WO 01/00247 | 1/2001 |
| WO | WO 01/68142 | * 9/2001 |

OTHER PUBLICATIONS

Bae M., et al.; Metalloprotease-specific Poly(ethylene glycol) Methyl Ether-Peptide-Doxonrubicin Conjugate for Targeting Anticancer Drug Delivery Based on Angiogenesis; Drug Exp. Clin. Res., 2003, vol. 29; No. 1, pp. 15-23.
Meers P.; Enzyme-activated targeting of liposomes; Advanced Drug Delivery Reviews 2001; vol. 53, pp. 265-272.
Miyazaki K., et al.; Sosetsu, Matrix Metalloproteinase; their structures and functions, with special reference to their roles in tumor invasion and metastasis; Seikagaku, Dec. 25, 1996; vol. 68; No. 12, pp. 1791-1807.

* cited by examiner

*Primary Examiner*—Sandra E. Saucier
*Assistant Examiner*—Lora E Barnhart
(74) *Attorney, Agent, or Firm*—Townsend and Townsend and Crew LLP

(57) ABSTRACT

The present invention relates to conjugates of a lipid, substrate peptide of an enzyme secreted from the cells of mammals, including humans, and a water-soluble polymer that can be used as colloidal carriers and the like of tissue-specific drug delivery systems, methods of producing these conjugates, peptide-water-soluble polymer conjugates optionally having protective groups that are useful as the intermediates of these conjugates, colloidal carriers made from these conjugates, and tissue-specific drug delivery systems that use these colloidal carriers.

13 Claims, 4 Drawing Sheets

```
                          SEQUENCE LISTING

<160> NUMBER OF SEQ ID NOS: 42

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 1

Pro Gln Gly Ile Ala Gly Trp
 1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 2

Pro Leu Gly Met Trp Ser Arg
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 3

Pro Leu Gly Val Arg Gly
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 4

Pro Leu Gly Leu Ala Gly
 1               5
```

```
<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 5

Pro Leu Gly Tyr Leu Gly
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 6

Pro Gln Gly Ile Ala Gly Arg
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 7

Pro Gln Gly Ile Ala Gly Gln
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 8

Pro Gln Gly Ile Ala Gly Thr
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 9

Pro Gln Gly Leu Ala Gly Gln
  1               5
```

```
<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 10

Pro Leu Gly Ile Ala Gly Gln
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 11

Pro Leu Gly Ile Ala Gly Pro
 1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 12

Pro Leu Gly Leu His Ala Arg
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 13

Pro Leu Gly Leu Trp Ala Arg
 1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 14

Pro Leu Ala Phe Trp Ala Arg
```

-continued

```
1               5
```

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 15

Pro Gln Gln Phe Phe Gly Leu
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 16

Gly Pro Gln Gly Ile Ala Gly Trp Gly
 1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 17

Gly Pro Leu Gly Ile Ala Gly Gln Gly
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 18

Gly Pro Gln Gly Ile Trp Gly Gln Gly
 1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate peptide,
      Gly-introduced functionally equivalent modified peptide,
      prostate-specific antigen (PSA) serine protease substrate
<220> FEATURE:
<221> NAME/KEY: MOD_RES
<222> LOCATION: (2)

```
<223> OTHER INFORMATION: Xaa = hydroxyproline (Hyp)
<220> FEATURE:
<221> NAME/KEY: MOD_RES
<222> LOCATION: (5)
<223> OTHER INFORMATION: Xaa = cyclohexylglycine (Chg)

<400> SEQUENCE: 19

Gly Xaa Ala Ser Xaa Gln Ser Leu Gly
 1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence:matrix
      metalloprotease (MMP)-related enzyme substrate
      peptide, Gly-introduced functionally equivalent
      modified peptide

<400> SEQUENCE: 20

Gly Pro Gly Arg Val Val Gly Gly Gly
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GPQGIAGWG peptide conjugate
<220> FEATURE:
<221> NAME/KEY: MOD_RES
<222> LOCATION: (1)
<223> OTHER INFORMATION: Xaa = 9-fluorenylmethyloxycarbonyl
      (Fmoc) conjugated to Gly

<400> SEQUENCE: 21

Xaa Pro Gln Gly Ile Ala Gly Trp Gly
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GPQGIAGWG-PEG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 22

Xaa Pro Gln Gly Ile Ala Gly Trp Xaa
 1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence:synthetic
      DSPE-GPQGIAGWG-PEG peptide conjugate
<220> FEATURE:
```

-continued

```
<221> NAME/KEY: MOD_RES
<222> LOCATION: (1)
<223> OTHER INFORMATION: Xaa = distearoyl phosphatidylethanolamine-
      glutaryl (DSPE) conjugated to Gly
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 23

Xaa Pro Gln Gly Ile Ala Gly Trp Xaa
 1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:synthetic
      GPQGIAGWG-PEG peptide conjugate
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 24

Gly Pro Gln Gly Ile Ala Gly Trp Xaa
 1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GPLGIAGQG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly

<400> SEQUENCE: 25

Xaa Pro Leu Gly Ile Ala Gly Gln Gly
 1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GPLGIAGQG-PEG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 26

Xaa Pro Leu Gly Ile Ala Gly Gln Xaa
 1               5

<210> SEQ ID NO 27
```

```
<211> LENGTH: 9
<212> TYPE: PRT
<213> ORGANISM: Artificial Sequence
<220> FEATURE:
<223> OTHER INFORMATION: Description of Artificial Sequence:synthetic
      GPLGIAGQG-PEG peptide conjugate
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 27

Gly Pro Leu Gly Ile Ala Gly Gln Xaa
  1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:synthetic
      DSPE-GPLGIAGQG-PEG peptide conjugate
<220> FEATURE:
<221> NAME/KEY: MOD_RES
<222> LOCATION: (1)
<223> OTHER INFORMATION: Xaa = distearoyl phosphatidylethanolamine-
      glutaryl (DSPE) conjugated to Gly
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 28

Xaa Pro Leu Gly Ile Ala Gly Gln Xaa
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GPQGIWGQG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly

<400> SEQUENCE: 29

Xaa Pro Gln Gly Ile Trp Gly Gln Gly
  1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GPQGIWGQG-PEG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)
```

-continued

```
<400> SEQUENCE: 30

Xaa Pro Gln Gly Ile Trp Gly Gln Xaa
  1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence:synthetic
      GPQGIWGQG-PEG peptide conjugate
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 31

Gly Pro Gln Gly Ile Trp Gly Gln Xaa
  1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence:synthetic
      DSPE-GPQGIWGQG-PEG peptide conjugate
<220> FEATURE:
<221> NAME/KEY: MOD_RES
<222> LOCATION: (1)
<223> OTHER INFORMATION: Xaa = distearoyl phosphatidylethanolamine-
      gluraryl (DSPE) conjugated to Gly
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 32

Xaa Pro Gln Gly Ile Trp Gly Gln Xaa
  1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence:synthetic
      Fmoc-GHypASChgQSLG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (2)
<223> OTHER INFORMATION: Xaa = hydroxyproline (Hyp)
<220> FEATURE:
<221> NAME/KEY: MOD_RES
<222> LOCATION: (5)
<223> OTHER INFORMATION: Xaa = cyclohexylglycine (Chg)

<400> SEQUENCE: 33

Xaa Xaa Ala Ser Xaa Gln Ser Leu Gly
  1               5

<210> SEQ ID NO 34
<211> LENGTH: 9
<212> TYPE: PRT
```

```
<213> ORGANISM: Artificial Sequence
<220> FEATURE:
<223> OTHER INFORMATION: Description of Artificial Sequence:sythetic
      Fmoc-GHypASChgQSLG-PEG peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (2)
<223> OTHER INFORMATION: Xaa = hydroxyproline (Hyp)
<220> FEATURE:
<221> NAME/KEY: MOD_RES
<222> LOCATION: (5)
<223> OTHER INFORMATION: Xaa = cyclohexylglycine (Chg)
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 34

Xaa Xaa Ala Ser Xaa Gln Ser Leu Xaa
  1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:synthetic
      GHypASChgQSLG-PEG peptide conjugate
<220> FEATURE:
<221> NAME/KEY: MOD_RES
<222> LOCATION: (2)
<223> OTHER INFORMATION: Xaa = hydroxyproline (Hyp)
<220> FEATURE:
<221> NAME/KEY: MOD_RES
<222> LOCATION: (5)
<223> OTHER INFORMATION: Xaa = cyclohexylglycine (Chg)
<220> FEATURE:
<221> NAME/KEY: MOD_RES
<222> LOCATION: (9)
<223> OTHER INFORMATION: Xaa = Gly conjugated to amidopropyl
      polyoxyethylene methyl ether (PEG)

<400> SEQUENCE: 35

Gly Xaa Ala Ser Xaa Gln Ser Leu Xaa
  1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence:synthetic
      DSPE-GHypASChgQSLG-PEG peptide conjugate
<220> FEATURE:
<221> NAME/KEY: MOD_RES
<222> LOCATION: (1)
<223> OTHER INFORMATION: Xaa = distearoyl phosphatidylethanolamine-
      glutaryl (DSPE) conjugated to Gly
<220> FEATURE:
<221> NAME/KEY: MOD_RES
<222> LOCATION: (2)
<223> OTHER INFORMATION: Xaa = hydroxyproline (Hyp)
<220> FEATURE:
<221> NAME/KEY: MOD_RES
<222> LOCATION: (5)
<223> OTHER INFORMATION: Xaa = cyclohexylglycine (Chg)
<220> FEATURE:
<221> NAME/KEY: MOD_RES
<222> LOCATION: (9)
```

<223> OTHER INFORMATION: Xaa = Gly conjugated to amidopropyl
     polyoxyethylene methyl ether (PEG)

<400> SEQUENCE: 36

Xaa Xaa Ala Ser Xaa Gln Ser Leu Xaa
 1               5

<210> SEQ ID NO 37
<211> LENGTH: 31
<212> TYPE: PRT
<213> ORGANISM: Artificial Sequence
<220> FEATURE:
<223> OTHER INFORMATION: Description of Artificial Sequence:synthetic
      GPQGIAGWG-PBLA peptide conjugate
<220> FEATURE:
<221> NAME/KEY: MOD_RES
<222> LOCATION: (10)..(31)
<223> OTHER INFORMATION: Xaa = benzyl-L-aspartate
<220> FEATURE:
<221> NAME/KEY: MOD_RES
<222> LOCATION: (31)
<223> OTHER INFORMATION: benzyl-L-aspartate at position 31 may be
      present or absent

<400> SEQUENCE: 37

Gly Pro Gln Gly Ile Ala Gly Trp Gly Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Description of Artificial Sequence:synthetic
      Fmoc-GPQGIAGWG-PBLA peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (10)..(31)
<223> OTHER INFORMATION: Xaa = benzyl-L-aspartate
<220> FEATURE:
<221> NAME/KEY: MOD_RES
<222> LOCATION: (31)
<223> OTHER INFORMATION: benzyl-L-aspartate at position 31 may be
      present or absent

<400> SEQUENCE: 38

Xaa Pro Gln Gly Ile Ala Gly Trp Gly Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Description of Artificial Sequence:synthetic
      GPQGIWGQG-PBLA peptide conjugate
<220> FEATURE:
<221> NAME/KEY: MOD_RES
<222> LOCATION: (10)..(31)
<223> OTHER INFORMATION: Xaa = benzyl-L-aspartate
<220> FEATURE:
<221> NAME/KEY: MOD_RES

```
<222> LOCATION: (31)
<223> OTHER INFORMATION: benzyl-L-aspartate at position 31 may be
      present or absent

<400> SEQUENCE: 39

Gly Pro Gln Gly Ile Trp Gly Gln Gly Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Description of Artificial Sequence:synthetic
      DODASuc-GPQGIAGWG-PHEA peptide conjugate
<220> FEATURE:
<221> NAME/KEY: MOD_RES
<222> LOCATION: (1)
<223> OTHER INFORMATION: Xaa = distearylamine-succinyl (DODASuc)
      conjugated to Gly
<220> FEATURE:
<221> NAME/KEY: MOD_RES
<222> LOCATION: (10)..(31)
<223> OTHER INFORMATION: Xaa = benzyl-L-aspartate
<220> FEATURE:
<221> NAME/KEY: MOD_RES
<222> LOCATION: (31)
<223> OTHER INFORMATION: benzyl-L-aspartate at position 31 may be
      present or absent

<400> SEQUENCE: 40

Xaa Pro Gln Gly Ile Ala Gly Trp Gly Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 41
<211> LENGTH: 31
<212> TYPE: PRT
<213> ORGANISM: Artificial Sequence
<220> FEATURE:
<223> OTHER INFORMATION: Description of Artificial Sequence:synthetic
      Fmoc-GPQGIWGQG-PBLA peptide conjugate
<220> FEATURE:
<221> NAME/KEY: MOD_RES
<222> LOCATION: (1)
<223> OTHER INFORMATION: Xaa = 9-fluorenylmethyloxycarbonyl (Fmoc)
      conjugated to Gly
<220> FEATURE:
<221> NAME/KEY: MOD_RES
<222> LOCATION: (10)..(31)
<223> OTHER INFORMATION: Xaa = benzyl-L-aspartate
<220> FEATURE:
<221> NAME/KEY: MOD_RES
<222> LOCATION: (31)
<223> OTHER INFORMATION: benzyl-L-aspartate at position 31 may be
      present or absent

<400> SEQUENCE: 41

Xaa Pro Gln Gly Ile Trp Gly Gln Gly Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 42
<211> LENGTH: 31
<212> TYPE: PRT
<213> ORGANISM: Artificial Sequence
```

```
<220> FEATURE:
<223> OTHER INFORMATION: Description of Artificial Sequence:synthetic
      DODASuc-GPQGIWGQG-PHEA peptide conjugate
<220> FEATURE:
<221> NAME/KEY: MOD_RES
<222> LOCATION: (1)
<223> OTHER INFORMATION: Xaa = distearylamine-succinyl (DODASuc)
      conjugated to Gly
<220> FEATURE:
<221> NAME/KEY: MOD_RES
<222> LOCATION: (10)..(31)
<223> OTHER INFORMATION: Xaa = hydroxyethyl-L-aspartate
<220> FEATURE:
<221> NAME/KEY: MOD_RES
<222> LOCATION: (31)
<223> OTHER INFORMATION: hydroxyethyl-L-aspartate at position 31 may be
      present or absent

<400> SEQUENCE: 42

Xaa Pro Gln Gly Ile Trp Gly Gln Gly Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30
```

LIPID-PEPTIDE-POLYMER CONJUGATES FOR LONG BLOOD CIRCULATION AND TUMOR SPECIFIC DRUG DELIVERY SYSTEMS

This application claims priority to U.S. Provisional Patent Application No. 60/439,560, filed Jan. 10, 2003, the disclosure of which is hereby incorporated by reference in its entirety.

TECHNICAL FIELD

The present invention relates to conjugates of a lipid, substrate peptide of an enzyme secreted from the cells of mammals, including humans, and a water-soluble polymer that can be used as colloidal carriers and the like of tissue-specific drug delivery systems, methods of producing these conjugates, peptide-water-soluble polymer conjugates optionally having protective groups that are useful as the intermediates of these conjugates, colloidal carriers made from these conjugates, and tissue-specific drug delivery systems that use these colloidal carriers.

PRIOR ART

Substances that have hydrophilic groups and lipophilic groups in one molecule are called amphipathic substances and form various molecular aggregates by mixing with water.

Spherical micelles, hexagonal structures, lamellar structures, hexagonal II structures, reversed micelle structures, and the like are molecular aggregates formed by amphipathic substances and their formation depends on the HLB (hydrophilic-lipophilic balance) of these substances.

Of these, liposomes having a lamellar structure comprise a lipid bilayer membrane containing an amphipathic substance that conveniently takes on a balance between hydrophilicity and lipophilicity. They are widely used as a carrier wherein a drug is encapsulated in a liposome and promise to improve drug efficacy by altering stability and distribution to tissue (Nojima et al. (editors), *Liposomes* (Nankodo Co., Ltd.)).

Nevertheless, there is a disadvantage in that liposomes are rapidly taken up by the reticuloendothelial system of the liver, spleen, and the like when administered intravenously. It is reported that long blood circulation can be acquired by preventing adsorption of blood proteins and the accompanying uptake by cells of the RES system, such as macrophages, by modifying the liposome surface with polyethylene glycol (PEG hereafter), ganglioside GM1, polyvinyl alcohol derivative, and the like, which are water-soluble polymers (*FEBS Letter*, 223, 42, 1987, *FEBS Letter*, 268, 253, 1990, Yakuzaigaku, 61, 86, 2001). In addition, particle diameter of the liposome has a strong effect on blood retention and it is possible to prevent uptake by the RES and thereby greatly improve blood retention by making the particle diameter 400 nm or smaller (Pharm. Res., 13, 1704, 1996).

Furthermore, PEG-modified liposomes with this type of blood retention have the property of extravasation from the blood stream and accumulating in tumor tissue as a result of an enhanced permeability and retention effect (EPR) (*Cancer Res.*, 46, 6387, 1986). PEG-modified liposomal doxorubicin has been encapsulated have already been marketed in Europe and the US for indications of Kaposi's sarcoma and breast cancer and their utility in terms of reducing adverse effects and clinical results is being reported (*Drugs*, 53, 520, 1997).

Nevertheless, it is reported based on the results of studies in tumor-bearing mice that there is not necessarily a correlation between accumulation of drug-encapsulated PEG-modified liposomes and antitumor activity. A major reason for this appears to be that interaction with the target cells is reduced by the PEG molecules present on the liposome surface and as a result, drug delivery to the cells is compromised (*Clin. Cancer, Res.*, 5, 3645, 1999).

Many attempts have been made to improve interaction between PEG-modified liposomes and the target cells in order to solve such disadvantages of PEG-modified liposomes. For instance, PEG-modified immunoliposomes where tumor cell-specific antibody is conjugated at the liposome membrane surface and pendant-type PEG-modified immunoliposome wherein antibody is conjugated at the end of the PEG molecule are reported in *Biochim. Biophys. Acta.*, 1234, 74–80, 1995. Problems still remain with the widespread use of this technology because it employs antibody.

On the other hand, liposomes that have at their surface hydrophilic segments that are effective for specific binding to a biological surface and hydrophilic polymers that are effective for blocking interaction with this hydrophilic segment at a biological surface are disclosed in Japanese Kohyo Patent No. 2001-503396. By means of this method, specific binding with a cell surface is realized by allowing the hydrophilic polymer to effectively function until the desired in vivo distribution has been reached and then administering an isolation agent in order to isolate the hydrophilic polymer. Nevertheless, it is necessary to administer an isolation agent in order to isolate the hydrophilic polymer by this method and therefore, problems still remain with the effects and safety of the isolation agent during in clinical application. Moreover, a technology is disclosed in Japanese Kokai Patent No. Hei 10-287554 whereby the properties of liposomes are altered as a result of the hydrophilic polymer shedding from the liposome surface time-dependently after administration in vivo. Furthermore, PEG-modified fusogenic liposomes are disclosed in *Nature Biotechnology*, 17, 775, 1999 with which it is possible to regulate the membrane fusion rate by changing the alkyl chain length of the lipid segment of a conjugate of a polyethylene glycol and a lipid. Nevertheless, it is possible that the water-soluble polymer will be shedded before the liposome is delivered to the diseased site and there is a fear that satisfactory results will be kept from being realized with these technologies.

Furthermore, peptide-lipid conjugates that are decomposed into peptide and dioleoyl phosphoethanolamine (lipid) by an elastase that is expressed near the site of inflammation and liposomes with this conjugate as a structural component are disclosed in Advanced Drug Delivery Reviews, 53, 265–272, 2001. These liposomes have the characteristic of changing from anionic to cationic at a pH near neutrality as a result of the peptide segment being severed, and because of this characteristic, successfully fuse with the cell membrane and transmit their contents to the cytoplasm. Nevertheless, nothing has been said with regard to blood retention and, taking accumulation in target cells and so forth into consideration, it cannot be called a satisfactory technology and there is room for improvement. Moreover, the peptide chain that is used is short and there is the fear that when conjugated and so forth with another substance, the effect of the other substance will not allow the peptide portion to be severed.

Therefore, thus far there is no known technology with which there is accumulation of a water-soluble polymer in tumor tissue and with which good drug delivery to target cells is realized without a reduction in interaction with the target cells.

DISCLOSURE OF THE INVENTION

The purpose of the present invention is to propose conjugates with which it is possible to alter the properties of a pharmaceutical preparation by cleaving the water-soluble polymer that has modified the surface of the pharmaceutical preparation using an enzyme secreted to diseased sites in order to improve clinical effects of the drug encapsulated in the pharmaceutical preparation, methods of producing these conjugates, conjugates that are useful as intermediates of these conjugates, colloidal carriers comprising these conjugates, and tissue-specific drug delivery systems that use these colloidal carriers.

It was discovered that metastatic tumor cells secrete enzymes that degrade type IV collagen at tumor sites (*Nature*, 284, 67, 1980) and thereafter, matrix metalloproteases (MMP hereafter) were ascertained, one after another, as enzymes that are secreted in tumors or sites of inflammation (*Seikagaku*, 68, 1791, 1996). It is reported that interstitial collagenase (MMP-1), gelatinase-A (MMP-2), gelatinase-B (MMP-9), stromelysin-1 (MMP-3), stromelysin-2 (MMP-10), stromelysin-3 (MMP-11), matrilysin (MMP-7), metalloelastase (MMP-12), and MMP-26 participate to a considerable degree in the invasion and metastasis of tumor cells and are activated at the surface of tumor cells (*Cancer Res.*, 55, 3263, 1995, *Seikagaku*, 68, 1791, 1996, *J. Biol. Chem.*, 277, 35168, 2002).

In light of these circumstances, the inventors focused their attention on substrate peptides of MMPs secreted by tumors or at sites of inflammation as enzymes that are secreted at diseased sites and synthesized conjugates wherein these peptides had been modified by water-soluble polymer and lipid and studied the properties of these conjugates. As a result, they completed the present invention upon discovering that these conjugates do not lose their properties during conjugation and retain their enzyme specificity, enzymatic degradation rate, and the like, and further, formulation as a colloidal carrier is possible using this lipid-peptide-water-soluble polymer conjugate.

By means of the present invention, it is possible to specifically shed the water-soluble polymer from the pharmaceutical preparation composed of a lipid, a substrate peptide of an enzyme secreted in tumors or sites of inflammation, and a water-soluble polymer in the target diseased site, such as tumor or inflammation, once the pharmaceutical preparation has reached the target disease site. In addition, it is possible to realize drug delivery to target cells by altering the properties of the pharmaceutical preparation by shedding the water-soluble polymer from the pharmaceutical preparation.

The names and symbols of the conjugates and the substances relating to these conjugates that are used in the present invention are listed below:

I. Conjugates of lipids, peptides and water-soluble polymers
  I-a. Lipid-peptide-water-soluble polymer conjugates
  I-b. Water-soluble polymer-peptide-lipid conjugates
II. Conjugates of water-soluble polymers and peptides
  II-a. Peptide-water-soluble polymer conjugates whose N-terminal end is optionally activated and optionally having protective groups at the functional groups other than the N-terminal end
  II-b. Water-soluble polymer-peptide conjugates whose C-terminal end is optionally activated and optionally having protective groups at the functional groups other than the C-terminal end
III. Lipids
  III-a. Lipids optionally substituted with carboxylic anhydride residue and whose carboxyl groups are optionally activated
  III-b. Lipids comprising optionally activated amino groups
IV. Peptides
  IV-a. Peptides whose C-terminal end is optionally activated and optionally having protective groups at the functional groups other than the C-terminal end
  IV-b. Peptides whose N-terminal end is optionally activated and optionally having protective groups at the functional groups other than the N-terminal end
V. Water-soluble polymers
  V-a. Water-soluble polymers selected from the group consisting of polyethylene glycols, polyamino acids, polyhydroxyethylamino acids, and polyvinyl pyrrolidones comprising functional groups that react with the carboxyl groups of peptides or their activating groups and whose one end is optionally substituted with methoxy groups and whose other end is optionally substituted with activating groups selected from —$NH_2$ or -lower alkyl-$NH_2$
  V-b. Water-soluble polymers selected from the group consisting of polyethylene glycol, polyamino acids, polyhydroxyethylamino acids, and polyvinyl pyrrolidones whose one end is optionally substituted with methoxy groups and whose other end is optionally substituted with activating groups selected from the group consisting of —CO-lower akylene-COO-dicarboxylic acid imidyl, -lower alkylene-COO-dicarboxylic acid imidyl, and -lower alkyl-dicarboxylic acid imidyl
VI. Conjugates of peptides and water-soluble polymers optionally having protective groups (production intermediates)
  VI-a. Peptide-water-soluble polymer conjugates optionally having protective groups
  VI-b. Water-soluble polymer-peptide conjugates optionally having protective groups
VII. Conjugates of lipids and peptides
  VII-a. Lipid-peptide conjugates whose C-terminal end is optionally activated and optionally having protective groups at the functional groups other than the C-terminal end
  VII-b. Lipid-peptide conjugates whose N-terminal end is optionally activated and optionally having protective groups at the functional groups other than the N-terminal end
VIII. Conjugates of lipids and peptides
  VIII-a. Lipid-peptide conjugates optionally having protective groups
  VIII-b. Lipid peptide conjugates optionally having protective groups That is, the present invention relates to
1. Conjugates (I) of A, B, and C, wherein A and C are conjugated at either end of B by peptide bonds, with
A being a lipid selected from the group consisting of phospholipids, higher fatty acids, higher aliphatic amines, glycolipids, ceramides, cholesterols, glycerides, and their derivatives,
B being a substrate peptide of an enzyme secreted from the cells of mammals, including humans, and C being a water-soluble polymer selected from the group consisting of polyethylene glycols, polyamino acids, polyhydroxyethylamino acids, and polyvinyl pyrrolidones whose one end is optionally substituted with methoxy groups and whose other end is optionally substituted with activating groups selected from the group consisting of —NH2,-lower alkyl-NH2,—CO -lower alkylene-COO-dicarboxylic acid imidyls, -lower alkylene-COO-dicarboxylic acid imidyls, and -lower alkyl-dicarboxylic acid imidyls, 2. the conjugates according to above-mentioned 1, wherein the conjugate of A, B, and C is A-B-C (I-a), 3. the conjugates according to above-mentioned 1, wherein the conjugate of A, B, and C is C-B-A (I-b), 4. the conjugates according to above-mentioned 1, wherein the substrate peptide of an enzyme is a substrate peptide of an enzyme selected from the group consisting of matrix metalloprotease, serine protease, cysteine protease, and aspartic protease, 5. the conjugates according to above-mentioned 4, wherein the substrate peptide of an enzyme is a substrate peptide of matrix metalloprotease, 6. the conjugates according to above-mentioned 5, wherein the substrate peptide of an enzyme is the substrate peptide of MMP-1, MMP-2, MMP-3, MMP-7, MMP-9, MMP-10, MMP-11, MMP-12, or MMP-26, 7. the conjugates according to above-mentioned 1, wherein the substrate peptide of an enzyme has the amino acid sequence shown by the following general formula (IX):

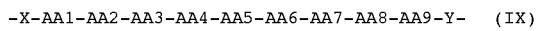

```
-X-AA1-AA2-AA3-AA4-AA5-AA6-AA7-AA8-AA9-Y-    (IX)
```

(The symbols in the sequence are defined below.
bond, carbonic anhydride residue, or one to five amino acid residues,
AA1: bond, or Gly residue,
AA2: Pro residue or Hyp residue,
AA3: Leu, Gln, Ala, or Gly residue,
AA4: Gly, Ala, Gln, or Ser residue
AA5: amino acid residue
AA6: amino acid residue,
AA7: Gly, Ser, or Ala residue
AA8: bond, or amino acid residue,
AA9: bond, imino group (—NH—), -lower alkylene-imino group, or Gly residue,
Y: bond, or one to five amino acid residues), 8. the conjugates according to above-mentioned 7, wherein the amino acid when X and/or Y each individually show an amino acid residue is a natural amino acid residue, the AA5 amino acid residue is an amino acid residue selected from the group consisting of Ile, Met, Val, Leu, Tyr, Chg, Val, and Phe residue, the AA6 amino acid residue is an amino acid residue selected from the group consisting of Ala, Trp, Arg, Leu, His, Gln, Val, and Phe residue, and the amino acid residue when AA8 is an amino acid residue is an amino acid residue selected from the group consisting of Trp, Arg, Gln, Thr, Pro, Gly, and Leu, 9. the conjugates according to above-mentioned 8, wherein the substrate peptide of an enzyme is a substrate peptide that contains the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NQ:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20 and shows activity as an enzyme substrate of matrix metalloprotease or serine protease, 10. the conjugates according to above-mentioned 4, wherein the substrate peptide of an enzyme is the substrate peptide of serine protease, 11. the conjugates according to above-mentioned 10, wherein the substrate peptide of an enzyme is the substrate peptide of prostate-specific antigen, urokinase-type plasminogen activator, tissue-type plasminogen activator, plasmin, trypsin, or tissue kallikrein, 12. conjugates of B and C, wherein B and C are conjugated by peptide bonds, with
B being a substrate peptide of an enzyme secreted from the cells of mammals, including humans, and
C being a water-soluble polymer selected from the group consisting of polyethylene glycols, polyamino acids, polyhydroxyethylamino acids, and polyvinyl pyrrolidones whose one end is optionally substituted with methoxy groups and whose other end is optionally substituted with activating groups selected from the group consisting of —NH$_2$,-lower alkyl-NH$_2$,—CO -lower alkylene-COO-dicarboxylic acid imidyls, -lower alkylene-COO-dicarboxylic acid imidyls, and -lower alkyl-dicarboxylic acid imidyls, 13. a colloidal carrier comprising a conjugate (I) according to above-mentioned 1, 14. the colloidal carrier according to above-mentioned 13, wherein the pharmaceutical is in the form of liposomes, emulsions, micelles, or nanoparticles, 15. the colloidal carrier according to above-mentioned 14, wherein the conjugate (I) content is 0.01 to 100 mol %, 16. tissue-specific drug delivery systems, which comprise a drug and a colloidal carrier of a conjugate (I) according above-mentioned 13, and are made such that the drug that is carried is emitted to the target tissue as a result of the enzyme substrate peptide segment of the above-mentioned conjugate being severed in response to an enzyme that is specifically secreted from diseased tissue.

The conjugates, methods of producing these conjugates, conjugates as intermediates of these conjugates, colloidal carriers comprising these conjugates, and tissue-specific drug delivery systems that use these colloidal carriers will now be described in detail.

The lipid used in the present invention means a substance having long-chain fatty acids or similar hydrocarbon chains in its molecules that is present in organisms or is derived from organisms, and there are no special restrictions as long as it is a lipid that is used as a component that forms the above-mentioned conjugate. It should be noted that what is cited as a "lipid" in the conjugate means a lipid residue to which the above-mentioned lipid has bonded. The same is true for the peptide and the water-soluble polymer. Phospholipids, fatty acids, glycolipids, glycerides, cholesterols, and their derivatives are cited as examples of this lipid.

Phosphatidylcholines, such as egg yolk phosphatidylcholine, hydrogenated egg yolk phosphatidylcholine, soybean phosphatidylcholine, hydrogenated soybean phosphatidylcholine, dilauroyl phosphatidylcholine, dimyristoyl phosphatidylcholine, dioleoyl phosphatidylcholine, dipalmitoyl phosphatidylcholine, and distearoyl phosphatidylcholine; phosphatidylethanolamines, such as egg yolk phosphatidylethanolamine, soybean phosphatidylethanolamine, dilauroyl phosphatidylethanolamine, dimyristoyl phosphatidylethanolamine, dioleoyl phosphatidylethanolamine, dipalmitoyl phosphatidylethanolamine, and distearoyl phosphatidylethanolamine; phosphatidylglycerols, such as egg yolk phosphatidylglycerol, dilauroyl phosphatidylglycerol, dimyristoyl phosphatidylglycerol, dioleoyl phosphatidylglycerol, dipalnitoyl phosphatidylglycerol, and distearoyl phosphatidylglycerol; phosphatidylinositols, such as hydrogenated egg yolk phosphatidylinositol, soybean phosphatidylinositol, dilauroyl phosphatidylinositol, dimyristoyl phosphatidylinositol, dioleoyl phosphatidylinositol, dipalmitoyl phosphatidylinositol, and distearoyl phosphatidylinositol; phosphatidylserines, such as dilauroyl phosphatidylserine, dimyristoyl phosphatidylserine, dioleoyl phosphatidylserine, dipalmitoyl phosphatidylserine, and distearoyl phosphatidylserine; phosphatidic acids, such as dilauroyl phosphatidic acid, dimyristoyl phosphatidic acid, dioleoyl phosphatidic acid, dipalmitoyl phosphatidic acid, and distearoyl phosphatidic acid; cardiolipins, such as tetralauroyl cardiolipin, tetramyristoyl cardiolipin, tetraoleoyl cardiolipin, tetrapalmitoyl cardiolipin, and tetrastearoyl cardiolipin; sphingomyelins; and their derivatives are cited as phospholipids. Fatty acids, such as lauric acid, myristic acid, oleic acid, palmitic acid, and stearic acid; aliphatic amines, such a laurylamine, myristylamine, palmitylamine, oleoylamine, stearylamine, dilaurylamine, dimyristylamine, dipalmitylamine, dioleoylamine, and distearylamine; aliphatic alcohols, such as lauryl alcohol, myristyl alcohol, oleoyl alcohol, palmityl alcohol, and stearyl alcohol; and their derivatives and salts are cited as fatty acids.

Ceramide, sphingosine, ganglioside, and their derivatives are cited as glycolipids.

Fatty acid glycerides, for instance, dilauryol glycerol, dimyristoyl glycerol, dioleoyl glycerol, dipalmitoyl glycerol, and distearoyl glycerol are cited as glycerides. Aliphatic dimethylammoniumpropane, for instance, dimyristoyl dimethylammoniumpropane, dioleoyl dimethylammoniumpropane, dipalmitoyl dimethylammonium propane, distearoyl dimethylammoniumpropane, and dioleoyloxy dimethylaminopropane hydrochloride; aliphatic trimethylammoniumpropanes, for instance, dimyristoyl trimethylammonium propane, dioleoyl trimethylammonium propane, dipalmitoyl trimethylammoniumpropane, and distearoyl trimethylammonium propane; and their derivatives can be cited as aliphatic dimethylammonium propanes.

Cholesterol and its derivatives are cited as cholesterols.

Of these, distearoyl phosphatidylethanolamine, dipalmitoyl phosphatidylethanolamine, dimyristoyl phosphatidylethanolamine, dioleoyl phosphatidylethanol amine, dilauroyl phosphatidylserine, dimyristoyl phosphatidylserine, dioleoyl phosphatidylserine, dipalmitoyl phosphatidylserine, distearoyl phosphatidylserine, laurylamine, myristylamine, palmitylamine, oleoylamine, stearylamine, dilaurylamine, dimyristylamine, dipalmitylamine, dioleoylamine, and distearylamine are preferred, dipalmitoyl phosphatidylethanolamine, distearoyl phosphatidylethanolamine, dipalmitylamine, and distearylamine are particularly preferred, and dipalmitoyl phosphatidylethanolamine and distearoyl phosphatidylethanoleamine are ideal.

There are no special restrictions to the peptide residue comprising the conjugates of the present invention as long as it is an enzyme substrate peptide residue that cleaves in response to an enzyme that is specifically secreted from diseased tissue of mammals, including humans. A residue of an enzyme substrate peptide is used with which it is possible to obtain a tissue-specific drug delivery system comprising a colloidal carrier, which in turn comprises a conjugate of the present invention containing this type of enzyme substrate peptide residue, and drug, and that is made such that the supported drug is delivered to the target tissue as a result of the enzyme substrate peptide segment of the above-mentioned conjugate being cleaved in response to an enzyme that is specifically secreted from diseased tissue.

Substrate peptides of enzymes that are secreted at tumor tissue and/or sites of inflammation and residue of modified peptides with the same effects wherein several (preferably one to three) of amino acids have been substituted, deleted, or inserted in the above-mentioned peptides are particularly preferred examples of this type of enzyme substrate peptide residue, and enzyme substrate peptides whose enzyme substrate peptide residue cleave in response to matrix metalloproptease, serine proteases, cysteine proteases, and aspartic proteases, residue of their functionally equivalent modified peptides, that is, substrate peptides of matrix metalloproteases or substrate peptides of serine proteases, and residue of their equivalent modified peptides, are ideal. Residue of enzyme substrate peptides of MMP-1, MMP-2, MMP-3, MMP-7, MMP-9, MMP-10, MMP-11, MMP-12, and MMP-26, residue of their functionally equivalent modified peptides, and substrate peptides of prostate-specific antigen, urokinase plasminogen activator, tissue-type plasminogen activator, plasmin, trypsin, and tissue kallikrein are particularly preferred as residue of enzyme substrate peptides.

Moreover, it is preferred that the peptide chain is long enough that it is unaffected by the water-soluble polymer such that severing of the peptide chain is facilitated. Specifically, 5 to 19 amino acids are preferred and 6 to 14 amino acids are particularly preferred. Nine amino acids are ideal.

When the formula of this type of residue is shown in relation to matrix metallo proteases (MMPs), residue represented by the following general formula (IX) are cited:

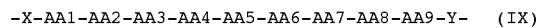

-X-AA1-AA2-AA3-AA4-AA5-AA6-AA7-AA8-AA9-Y-     (IX)

(The symbols in the sequence are defined below.
X: bond, carboxylic anhydride residue, or one to five amino acid residues,
AA1: bond, or Gly residue,
AA2: Pro residue,
AA3: Leu or Gln residue,
AA4: Gly, Ala, or Gln residue
AA5: amino acid residue
AA6: amino acid residue,
AA7: Gly, Ser, or Ala residue
AA8: bond, or amino acid residue,
AA9: bond, imino group (—NH—), lower alkyleneimino group, or Gly residue,
Y: bond, or one to five amino acid residues)

Preferably the amino acid residue when X and/or Y each individually show an amino acid residue is a natural amino acid residue, the amino acid residue shown by AA5 is an amino acid residue selected from the group consisting of Ile, Met, Val, Leu, Tyr, Chg, Val, and Phe residue, the amino acid residue shown by AA6 is an amino acid residue selected from the group consisting of Ala, Trp, Arg, Leu, His, Gln, Val, and Phe residue, and the amino acid residue shown by AA8 is an amino acid residue selected from the group consisting of Trp, Arg, Gln, Thr, Pro, Gly, and Leu.

Of the many enzyme substrates known as MMP-related enzyme substrate peptides, residue of the MMP-related enzyme substrate peptides of SEQ ID NO:1 (Pro-Gln-Gly-Ile-Ala-Gly-Trp), SEQ ID NO:2 (Pro-Leu-Gly-Met-Trp-Ser-Arg), SEQ ID NO:3 (Pro-Leu-Gly-Val-Arg-Gly), SEQ ID NO:4 (Pro-Leu-Gly-Leu-Ala-Gly), SEQ ID NO:5 (Pro-Leu-Gly-Tyr-Leu-Gly), SEQ ID NO:6 (Pro-Gln-Gly-Ile-Ala-Gly-Arg), SEQ ID NO:7 (Pro-Gln-Gly-Ile-Ala-Gly-Gin), SEQ ID NO:8 (Pro-Gln-Gly-Ile-Ala-Gly-Thr), SEQ ID NO:9 (Pro-Gln-Gly-Leu-Ala-Gly-Gln), SEQ ID NO:10 (Pro-Leu-Gly-Ile-Ala-Gly-Gln), SEQ ID NO:1 1 (Pro-Leu-Gly-Ile-Ala-Gly-Pro), SEQ ID NO:12 (Pro-Leu-Gly-Leu-His-Ala-Arg), SEQ ID NO:13 (Pro-Leu-Gly-Leu-Trp-Ala- Arg), SEQ ID NO:14 (Pro-Leu-Ala-Phe-Trp-Ala-Arg), SEQ ID NO:15 (Pro-Gln-Gln-Phe-Phe-Gly-Leu), SEQ ID NO:16 (Gly-Pro-Gln-Gly-Ile-Ala-Gly-Trp-Gly), SEQ ID NO:17 (Gly-Pro-Leu-Gly-Ile-Ala-Gly-Gln-Gly), SEQ ID NO:18 (Gly-Pro-Gln-Gly-Ile-Trp-Gly-Gln-Gly), SEQ ID NO:19 (Gly-Hyp-Ala-Ser-Chg-Gln-Ser-Leu-Gly), and SEQ ID NO:20 (Gly-Pro-Gly-Arg-Val-Val-Gly-Gly-Gly), and functionally equivalent modified peptides of these peptides, particularly substrate peptides containing these sequences, having a Gly residue at one or both of the N-terminal end and/or C-terminal end, and showing activity as an enzyme substrate of matrix metalloprotease or serine protease (Gly-introduced functionally equivalent modified peptides), are preferred as the MMP-related enzyme substrate peptide residue of the present invention.

The peptide can be synthesized in accordance with solid-phase peptide synthesis methods. For instance, the carboxyl end of the amino group is linked by a covalent bond to a solid phase of insoluble resin and the peptide linkage is gradually extended to the amino end side in the same vessel. Purification of the intermediate is also performed in the same vessel during this time and when the peptide that is eventually needed has been synthesized, the desired peptide can be obtained by cleaving the peptide chain from the solid phase.

Polyalkylene glycols, polyamino acids, polyhydroxyalkyl amino acids, and vinyl polymers are cited as the water-soluble polymer used in the present invention.

Polymethylene glycol, polyethylene glycol, poly-n-propylene glycol, and poly-iso-propylene glycol are cited as polyalkylene glycols.

Polyalanine, polyarginine, polyasparagine, polyaspartic acid, polycystein, polyglutamine, polyglutamic acid, polyglycine, polyhystidine, polyisoleucine, polyleucine, polylysine, polymethionine, polyphenylalanine, polyproline, polyserine, polythreonine, polytryptophan, polytyrosine, polyvaline, and the like are cited as polyamino acids.

Polyhydroxymethyl amino acid, polyhydroxyethyl amino acid, polhydroxypropyl amino acid, and polyhydroxybutyl amino acid are cited as polyhydroxyalkyl amino acids, and polyhydroxyethyl aspartate, polyhydroxyethyl cystein, polyhydroxyethyl glutamate, and polyhydroxyethyl lysine are cited as specific examples of polyhydroxyalkyl amino acids.

Polyvinyl alcohol, polyvinyl methyl ether, polyvinyl pyrrolidone, polyvinyl oxazolidone, polyvinyl methyl oxazolidone, polyvinyl amine, poly-2-vinyl pyridine, poly-4-vinyl pyridine, poly-N-vinyl succinimide, poly-N-vinyl formamide, and poly-N-vinyl-N-methyl acetamide are cited as vinyl polymers.

Of these, polyethylene glycol, polyhydroxyethyl aspartate, polyhydroxyethyl glutamate, polyvinyl alcohol, and polyvinyl pyrrolidone are preferred, polyethylene glycol, polyhydroxyethyl aspartate, and polyhydroxyethyl glutamate are particularly preferred, and polyethylene glycol is ideal.

—OH, —O—CH$_3$, —CH$_2$CH$_2$—OH, —NH$_2$, —CH$_2$CH$_2$—NH$_2$, —(CH$_2$)$_3$—NH$_2$, —O—CH$_2$CH$_2$—NH$_2$, —O—(CH$_2$)$_3$—NH$_2$, —S—CH$_2$CH$_2$—NH$_2$, —O$_2$CNH—CH$_2$CH$_2$—NH$_2$, —OCO—CH (lower alkyl)-NH$_2$, —O—CH$_2$—CO—NH—NH$_3$Cl, —SH, —COOH, —OCO—CH$_2$CH$_2$—COOH, —O—CH$_2$—COOH, —O—CH$_2$CH$_2$—COOH, —OCO—NH—CH (lower alkyl)-COOH, —COO-dicarboxylic acid imidyl, —OCO—CH$_2$CH$_2$—COO-dicarboxylic acid imidyl, —NH—CO—CH$_2$CH$_2$—COO-dicarboxylic acid imidyl, —O—CH$_2$CH$_2$—COO-dicarboxylic acid imidyl, —O—CH$_2$—COO-dicarboxylic acid imidyl, —OCO—NH—CH (lower alkyl)-COO-dicarboxylic acid imidyl, —O—CH$_2$-epoxydyl, —OCO-imidazole, —OCO-nitrophenyl, —OSO$_2$—CH$_2$—CF$_3$, —O—CH$_2$CH$_2$—CHO, —O—CH$_2$CH$_2$—NCO, —O—CH$_2$CHCH$_2$, —O$_2$CCHCH$_2$, —O$_2$CC(CH$_3$)CH$_2$—SO$_2$—CHCH$_2$, —NH—CO—CH$_2$I, -maleimidyl, —S—S-orthopyridyl, and -biotin are cited as terminal end substitution groups of the water-soluble polymers.

The average molecular weight of the water-soluble polymer of the present invention is 150 to 50,000, preferably 200 to 15,000. An average molecular weight of 500 to 5,000 is ideal.

Maleic anhydride, succinic anhydride, citraconic anhydride, glutaric anhydride, acetic anhydride, phthalic anhydride, and the like are cited as carboxylic anhydrides used in the present invention.

The enzyme that is secreted from the cells of mammals, including humans, in the present invention means in particular an enzyme that is secreted at tumor tissue or a site of inflammation, and matrix metalloproteases, serine proteases, cysteine proteases, and aspartic proteases are cited as examples.

MMP-1, MMP-2, MMP-3, MMP-7, MMP-8, MMP-9, MMP-10, MMP-11, MMP-12, MMP-13, MMP-14, MMIP-15, MMP-16, MMP-17, MMP-18, MMP-19, MMP-20, MMIP-21, MMP-23, MMP-24, MMP-25, MMP-26, and MMP-28 are cited as examples of matrix metalloprotease. Prostate-specific antigen, urokinase-type plasminogen activator, tissue-type plasminogen activator, plasmin, trypsin, tissue kallikrein, chymotrypsin, cathepsin G, elastase, and thrombin are cited as examples of serine protease. Cathepsin B, cathepsin H, and cathepsin L are cited as cysteine protease. Cathepsin D and cathepsin E are cited as aspartic proteases.

(2) Methods of Producing the Conjugates of the Present Invention

Conjugates (I), particularly (I-a) and (I-b), of the present invention, as well as their intermediates can be produced by various conventional synthesis methods in accordance with their basic structure or type of substitution groups. There are cases where, depending on the type of functional groups at this time, protecting these functional groups with appropriate protective groups or substituting them with groups that can be easily converted to these functional groups is effective as a manufacturing technology. Amino groups, hydroxyl groups, and carboxyl groups are examples of such functional groups, and the protective groups in *Protective Groups in Organic Synthesis* (T. W. Greene and P. G. M. Wuts, Third Edition, 1999) can be cited as examples of these protective groups. These can be selected and used as necessary in accordance with the reaction conditions. The desired compound can be obtained by this method by introducing protective groups and performing the reaction and then removing the protective groups or converting them to the desired groups as necessary.

Conjugates (I) of a lipid, peptide, and water-soluble polymer of the present invention are produced by reacting peptide-water-soluble polymer conjugate (II-a) whose N-terminal end is optionally activated and optionally having protective groups at the functional groups other than the N-terminal end and lipid (III-a) optionally substituted with carboxylic anhydride residue and whose carboxyl groups are optionally activated, or reacting water-soluble polymer-peptide conjugate (II-b) whose C-terminal end is optionally activated and optionally having protective groups at the functional groups other than the C-terminal end and lipid (III-b) comprising optionally activated amino groups and then removing the protective groups as necessary.

Conjugates (I) of the present invention are also produced by reacting water-soluble polymer (V-a) selected from the group consisting of polyethylene glycols, polyamino acids, polyhydroxyethylamino acids, and polyvinyl pyrrolidones whose one end is optionally substituted with methoxy groups and whose other end is optionally substituted with groups selected from the group consisting of —$NH_2$, -lower alkyl-$NH_2$, —CO-lower alkylene-COO-dicarboxylic acid imidyl, -lower alkylene-COO-dicarboxylic acid imidyl, and -lower alkyl-dicarboxylic acid imidyl, or reacting water-soluble polymer (V-b) selected from the group consisting of polyethylene glycol, polyamino acids, polyhydroxyethylamino acids, and plyvinylpyrrolidones whose one end is optionally substituted with methoxy groups and whose other end is optionally substituted with groups selected from the group consisting of —$NH_2$, -lower alkyl-NH2, —CO-lower alkylene-COO-dicarboxylic imidyls, -lower alkylene-COO-dicarboxylic acid imidyls, and -lower alkyl-dicarboxylic acid imidyls, each optionally having its respective protective groups; and removing the protective groups as necessary.

Specifically, conjugates (I) of the present invention are divided into lipid-peptide-water-soluble polymer conjugates (I-a) and water-soluble polymer-peptide-lipid conjugates (I-b). These are described in detail below together with the methods of producing the starting compounds:

It is possible to select the production method from the four types of production methods listed below, production methods 1 through 4, each being divided into process 1 and process 2.

Production Method 1

Process 1

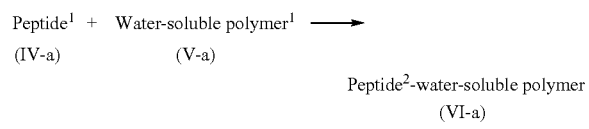

Process 2

Removal of N-terminal end protective groups, N-terminal end activation as necessary

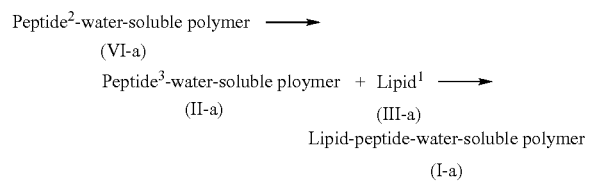

(In the formula, peptide$^1$ means a peptide whose C-terminal end is optionally activated and which optionally has protective groups at the functional groups other than the C-terminal end, water-soluble polymer$^1$ means a water-soluble polymer selected from the group consisting of polyethylene glycols, polyamino acids, polyhydroxyethylamino acids and polyvinyl pyrrolidones containing functional groups that will react with the carboxyl groups of the peptide or their activating groups and whose one end is optionally substituted with methoxy groups and whose other end is optonally substituted with activating groups selected from the group consisting of —$NH_2$ and -lower alkyl—$NH_2$ groups, peptide$^2$ means a peptide residue optionally having protective groups, peptide$^3$ means a peptide residue optionally having protective groups at the functional groups other than the N-terminal end, water-soluble polymer means a water-soluble polymer residue, lipid$^1$ means a lipid selected from the group consisting of phospholipids, higher fatty acids, higher aliphatic amines, glycolipids, seramides, cholesterols, glycerides, and their derivatives optionally substituted with carboxylic anhydride residue and whose carboxyl groups are optionally activated, lipid means a residue of a lipid selected from the group consisting of phospholipids, higher fatty acids, higher aliphatic amines, glycolipids, seramides, cholesterols, glycerides, and their derivatives optionally containing cleaved carboxylic anhydride residue as mediator groups, and peptide means peptide residue optionally having protective groups.)

Process 1

This reaction is the method whereby peptide-water-soluble polymer conjugate (VI-a) optionally having protective groups is obtained by reacting peptide (IV-a) whose C-terminal end is optionally activated and optionally having protective groups at the functional groups other than the C-terminal end and water-soluble polymer (V-a) selected from the group consisting of polyethylene glycols, polyamino acids, polhydroxyethylamino acids, and polyvinyl pyrrolidones whose one end is optionally substituted with methoxy groups and whose other end is optionally substituted with groups selected from the group consisting of —$NH_2$ and -lower-akyl-$NH_2$ groups.

Acid halides such as acid chlorides and acid bromides; esters such as acid azides, methyl esters, and ethyl esters; active esters such as N-hydroxysuccinimide (HONSu) and 1-hydroxybenzotriazole (HOBt); symmetric acid anhydrides; mixed acid anhydrides such as alkyl carbonates and p-toluenesulfonates; and the like are cited as the C-terminal end-active form of the peptide in process 1. On the other hand, the functional groups of the water-soluble polymer that are capable of reacting with the carboxyl group of the peptide or its activated group are typically amino groups. That is, when the water-soluble polymer is polyethylene glycol whose one end has methoxy groups, the other end has —$NH_2$, -lower alkyl-$NH_2$, and the like, when the water-soluble polymer is a polyamino acid or polyhydroxyethylamino acid, the other end is an optionally activated amino acid, and when the water-soluble polymer is a polyvinyl pyrrolidone, the other end is a pyrrolidone ring.

According to conventional methods, this reaction is performed by binding one of the starting compounds to a resin, and reacting the other starting compound, then removing the side product, and then separating the reaction product from the resin, or submitting the reaction product as is to the next process.

The reaction can be performed by condensation of peptide (IV-a) whose C-terminal end is optionally activated and which optionally has protective groups at the functional groups other than the C-terminal end and water-soluble polymer (V-a) optionally having methoxy groups or methoxy groups and activating groups in the presence of a condensation agent (for instance, dicyclohexylcarbodiimide (DCC), diisopropylcarbodiimide (DIPC), 1-ethyl-3-(3-dimethylaminopropyl)carbodiimide (WSC), 1,1'-carbonylbis-1H-imidazole (CDI), and the like), and depending on the case, other additives (for instance, N-hydroxysuccinimide (HONSu), 1-hydroxybenzotriazole (HOBt), and the like). Moreover, once it has been isolated, the active ester form of peptide (IV-a) and the above-mentioned additives can be condensed with water-soluble polymer (V-a).

The reaction conditions vary with the type of starting compound that is used, such as the type of active form, and the like. However, it is preferred that the reaction be performed using the equimolar amount or excess moles of one of starting compound (II-a) and (III-a) in an organic solvent that is inert to the reactions, such as an aromatic hydrocarbon, for instance, benzene, toluene, or xylene; an ether, for instance, diethyl ether, tetrahydrofurane (THF), 1,4-dioxane, or dimethoxyethane; a halogenated hydrocarbon, for instance, dichloromethane, 1,2-dichloroethane, or chloroform; N,N-dimethyl formamide (DMF); N-methyl-2-pyrrolidone (NMP); or pyridine. The solvents are used alone or as a mixture of two or more.

Moreover, depending on the type of active form, there are times when it is preferred that the reaction be conducted in the presence of a base, such as an organic base, for instance, trimethylamine, triethylamine, pyridine, picoline, lutidine, dimethyaniline, or N-methylmorpholine, or an inorganic base, such as potassium carbonate, sodium carbonate, sodium hydroxide, or potassium hydroxide. Pyridine can also serve as the solvent.

The reaction can usually be performed under ordinary temperature, but there are also cases where, depending on the type of starting compound, particularly the type of active form, it is performed under cold conditions or while heating.

Process 2

When peptide-water-soluble polymer conjugate (VI-a) optionally having protective groups that has been obtained by process 1 has protective groups at the N-terminal end, these protective groups are removed and this N-terminal end is activated as necessary to obtain peptide-water-soluble polymer conjugate (II-a) whose N-terminal end is optionally activated and which optionally has protective groups at the functional groups other than the N-terminal end.

Next, conjugates (I-a) of the present invention can be produced by reacting (II-a) with lipid (III-a) optionally substituted with carboxylic anhydride residue and whose carboxyl groups have optionally been activated and removing the protective groups as necessary. Peptide-water-soluble polymer conjugate (II-a) whose N-terminal end is optionally activated and optionally having protective groups at the functional groups other than the N-terminal end and lipid (III-a) optionally substituted with carboxylic anhydride residue and whose carboxyl groups are optionally activated are reacted and the protective groups are removed as necessary when there are protective groups.

Removal of the protective groups at the N-terminal end is performed by conventional methods. The protective groups can be easily removed by treating, for instance, protective groups of amino groups, such as acyl-type protective groups, including 9-fluorenylmethylcarbonyl groups, with piperidine/dimethylformamide. In addition, catalytic reduction is preferred when the protective groups of the N-terminal end are benzyloxycarbonyl groups, and depending on the case, treatment with an acid such as trifluoroacetic acid/hydrogen bromide, and the like is used. Furthermore, the above-mentioned acid treatment is preferred for other urethane-type protective groups, such as tert-butoxycarbonyl groups.

Acid addition salts of these amines and the like are cited as the activating groups of the N-terminal end. Moreover, the various protective groups in the above-mentioned non-patent references are cited as protective groups of functional groups other than the N-terminal end.

On the other hand, a lipid that has been substituted with carboxylic anhydride residue is used when the terminal end groups of the lipid, such as phosphatidylethanolamine, are functional groups, such as amino groups, and the carboxylic anhydride residue is bonded in order to facilitate bonding with the N terminal end of the peptide. Moreover, the same halides, acid azides, ordinary esters, active esters, symmetric acid anhydrides, and mixed acid anhydrides as given for the activating groups of the C-terminal end of the above-mentioned peptides are given as the optionally activated carboxylic acid residue of the lipid.

As with process 1, the reaction is a peptide conjugation reaction and it can be performed as process 1. That is, it can be performed by condensation of conjugate (II-a) and lipid (III-a) in the presence of a condensation agent and, depending on the case, the above-mentioned additives. Moreover, once it has been isolated, the active ester form of lipid (III-a) and above-mentioned additives can be condensed with conjugate (II-a).

This reaction can also be performed by binding one of the starting compounds to a resin in accordance with conventional methods.

As with process 1, the reaction conditions vary with the type of starting compound used, such as the type of active form, and the like, but it is preferred the reaction be performed using the equimolar amount or excess moles of one of starting compounds (II-a) and (III-a) in an organic solvent that is inert to the reaction. The solvents can be used alone or as a mixture of two or more.

Moreover, depending on the type of active form, there are times when it is preferred that the reaction be conducted in the presence of a base, such as an organic base, for instance, trimethylamine, triethylamine, pyridine, picoline, lutidine, dimethyaniline, or N-methylmorpholine, or an inorganic base, such as potassium carbonate, sodium carbonate, sodium hydroxide, or potassium hydroxide. Pyridine can also serve as the solvent.

The reaction can usually be performed under ordinary temperature, but there are also cases where, depending on the type of starting compound, particularly the type of active form, it is performed under cold conditions or while heating.

Removal of the protective groups is performed by conventional methods. For instance, when protective groups of amino groups are present, they can be easily removed by the above-mentioned piperidine/dimethyl formamide treatment, catalytic reduction, or acid treatment.

Furthermore, when protective groups of the carboxyl groups are present as protective groups, the protective groups can be easily removed by saponification when the protective groups are ester-forming groups, by catalytic reduction or saponification when they are benzyl groups or substituted benzyl groups, by the above-mentioned acid treatment when they are tert-butyl groups, and by contacting water when they are trimethylsilyl groups.

Protective groups of mercapto groups and hydroxyl groups can be removed for the most part by conventional sodium/liquid ammonia treatment, and depending on the type of protective group, they can also be easily removed by catalytic reduction (for instance, —O-benzyl) or hydrolysis in the presence of an acid or an alkali (for instance, acyl protective groups).

Production Method 2

Process 1

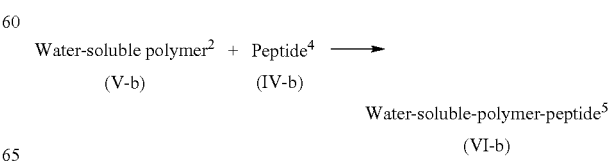

Process 2

Removal of C-terminal end protective groups, C-terminal end activation as necessary

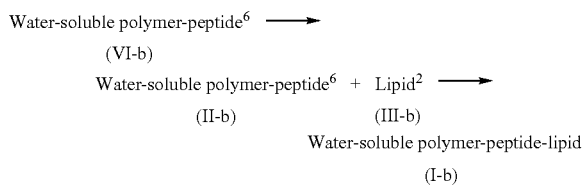

(In the formula, water-soluble polymer, peptide, and lipid are as defined above, water-soluble polymer$^2$ is a water-soluble polymer selected from the group consisting of polyethylene glycols, polyamino acids, polyhydroxyethylamino acids, and polyvinyl pyrrolidones whose one end is optionally substited with methoxy groups and whose other end is optionally substituted with groups selected from the group consisting of —CO-lower alkylene-COO-dicarboxylic acid imidyl, -lower alkylene-COO-dicarboxylic acid imidyl, and -lower alkyl-dicarboxylic acid imidyl, each optionally having its respective protective groups, peptide$^4$ is a peptide whose N-terminal end is optionally activated and which optionally has protective groups at the functional groups other than the N-terminal end, peptide$^5$ is peptide residue optionally having protective groups, peptide$^6$ is a peptide residue whose C-terminal end is optionally activated and which optionally has protective groups at the functoinal groups other than the C-terminal end, and lipid$^2$ is a lipid comprising optionally activated amino groups.)

Process 1

This reaction is the reactoin whereby water-soluble polymer-peptide conjugate (VI-b) optionally having protective groups is produced by reacting water-soluble polymer (V-b) selected from the group consisting of polyethylene glycols, polyamino acids, polyhydroxyethyl amino acids and polyvinyl pyrrolidones whose one end is optionally substituted with methoxy groups and whose other end is optionally substituted with groups selected from the group consisting of —CO-lower alkylene-COO-dicarboxylic acid imidyls, -lower alkylene-COO-dicarboxylic acid imidyls, and -lower alkyl-dicarboxylic acid imidyls, each optionally having its respective protective groups, and peptide (IV-b) whose N-terminal end is optionally activated and which optionally has protective groups at the functional groups other than the N-terminal end.

The above-mentioned protective groups of amino groups are cited as the optional protective groups of water-soluble polymer (V-a) selected from the group consisting of polyethylene glycols, polyamino acids, polyhydroxyethyl amino acids and polyvinyl pyrrolidones whose one end is optionally substitued with methoxy groups and whose other end is optionally substitued with groups selected from the group consisting of —CO-lower alkylene-COO-dicarboxylic acid imidyls, -lower alkylene-COO-dicarboxylic acid imidyls, and -lower alkyl-dicarboxylic acid imidyls, each optionally having its respective protective groups.

On the other hand, acid addition salts of this amine, and the like are cited as the activating groups of the N terminal of the peptide. Moreover, the protective groups in the above-mentioned non-patent references are cited as protective groups of the functional groups other than the N-terminal end of the peptide.

This reaction is the same peptide conjugation reaction as in production method 1 and it can be performed in the same way as production method 1.

Process 2

The reaction of process 2 is the reaction whereby water-soluble polymer-peptide-lipid conjugate (I-b) is produced, characterized in that the protective groups are removed from the water-soluble polymer-peptide conjugate (VI-b) optionally having protective groups that was obtained in process 1 when it has protective groups at its C-terminal end and the C-terminal end is activated as necessary to produce water-soluble polymer-peptide conjugate (II-b) whose C-terminal end is optionally activated and which optionally has protective groups at the functional groups other than the C-terminal end and then this is reacted with lipid (III-b) comprising optionally activated amino groups and the protective groups are removed as necessary.

Lipids comprising terminal amino groups such as phosphatidylethanolamine are cited as lipids comprising amino groups. Acid addition salts of this amine are cited as the active form in which the amino groups are optionally activated. Moreover, the activating groups listed in production method 1 are cited as the C-terminal end activating groups of the peptide.

This reaction is also a peptide conjugation reaction and it is preferred that it be performed in accordance with production method 1.

Production Method 3

Process 1

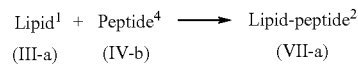

Process 2

Removal of C terminal protective groups, C-terminal end activation as necessary

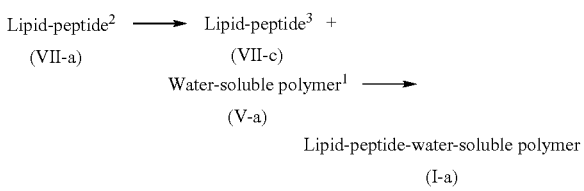

(In the formula, lipid, lipid$^1$, peptide, peptide$^2$, peptide$^3$, peptide$^4$, water-soluble polymer, and water-soluble polymer$^1$ are as previously defined.)

The present method comprises the reaction (process 1) whereby lipid-peptide conjugate (VIII-a) optionally having protective groups is produced by reacting lipid (III-a) optionally substituted with carboxylic anhydride residue and whose carboxyl groups are optionally activated and peptide (IV-b) whose N-terminal end is optionally activated and optionally having protective groups at the functional groups other than the N-terminal end; removing the protective groups when lipid-peptide conjugate (VIII-a) optionally having protective groups that has been obtained by process 1 has protective groups at the C-terminal end and optionally activating the C-terminal end as necessary to obtain lipid-peptide conjugate (VII-a) whose C-terminal end is optionally activated and optionally having protective groups at the functional groups other than the C-terminal end; then reacting this with water-soluble polymer (V-a) selected from the group consisting of polyethylene glycols, polyamino acids, polyhydroxyethylamino acids, and polyvinyl pyrrolidones whose one end is optionally substituted with methoxy groups and whose other end is substituted with —$NH_2$ or -lower alkyl-$NH_2$ groups; and removing the protective groups as necessary to produce lipid-peptide-water-soluble polymer conjugate (I-a) (process 2).

These reactions of this production method are also peptide conjugation reactions and they can be performed in accordance with production methods 1 and 2.

Production method 4
Process 1

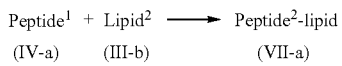

Process 2
Removal of N terminal protective groups, N-terminal end activation as necessary

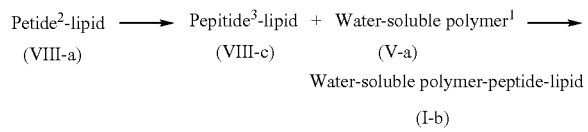

(In the formula, lipid, lipid$^2$, peptide, peptide$^1$, peptide$^3$, water-soluble polymer, and water-soluble polymer$^1$ are as previously defined.)

This reaction is the reaction whereby water soluble polymer-peptide-lipid conjugate (I-b) is produced, characterized in reacting peptide (IV-a) whose C-terminal end is optionally activated and optionally having protective groups at the functional groups other than the C-terminal end and lipid (III-b) comprising optionally activated amino groups; removing the protective groups when the peptide-lipid conjugate (VIII-b) optionally having protective groups that has been obtained has protective groups at the N-terminal end and activating the N-terminal end as necessary to produce lipid-peptide conjugate (VII-b) whose N-terminal end is optionally activated and optionally having protective groups at the functional groups other than the N-terminal end; then reacting this with water-soluble polymer (V-b) selected from the group consisting of polyethylene glycols, polyamino acids, polyhydroxyethylamino acids, and polyvinyl pyrrolidones whose one end is optionally substituted with methoxy groups and whose other end is optionally substituted with groups selected from the group consisting of —CO-lower alkylene-COO-dicarboxylic acid imidyls, -lower alkylene-COO-dicarboxylic acid imidyls, and -lower-alkyl-dicarboxylic acid imidyls, each optionally having its respective protective groups; and removing the protective groups as necessary.

This reaction is also a peptide conjugation reaction and it can be performed in accordance with production methods 1 through 3.

(3) Conjugates as Intermediates of Conjugate Preparations and their Production Methods The invention of "peptide-water-soluble polymer conjugates (VI-a) optionally having protective groups," which are novel intermediates that are useful in the production of conjugates (I) of a lipid, peptide, and water-soluble polymer of the present invention is also included in the inventions of the present application.

The definitions relating to the peptide residue and water-soluble polymer comprising production intermediates (VI-a) are the same as given above, and these production intermediates can be produced by process 1 of above-mentioned production method 1.

These production intermediates are intermediates for directly producing conjugates (I) of the present invention that are useful as excellent colloidal carriers, and the path that leads to conjugate (I), which is the final target substance, is as shown by process 2 of above-mentioned production method 1.

(4) Colloidal Carriers Comprising Conjugates

Colloidal carrier generally means a colloid vehicle capable of encapsulating low-molecular-weight substances or high-molecular-weight substances. Colloid means a dispersed phase or dispersed particles that although not visible under an optical microscope, are dispersed as particles that are larger than atoms or low-molecular-weight particles. Colloidal carrier specifically means liposomes, emulsions, micelles, nanoparticles, and the like. Consequently, the colloidal carrier comprising a conjugate in the present invention means liposomes, emulsions, micelles, or nanoparticles comprising a conjugate of a lipid, peptide and water-soluble polymer and other additives. A low-molecular-weight substance or high-molecular-weight substance, such as a drug, can be supported by using this colloidal carrier to successfully transport a drug and the like to the target diseased site, such as tumors or inflammation, and deliver the drug to the target cells by separation of the water-soluble polymer from the conjugate.

There are no special restrictions to the lipid that is used to prepare the colloidal carrier as long as it is a component that will form a colloidal carrier, such as liposomes, emulsions, micelles, or nanoparticles. Phospholipids, fatty acids, glycolipids, glycerides, cholesterols, and their derivatives are cited as examples of the lipid.

Phosphatidylcholines, such as egg yolk phosphatidylcholine, hydrogenated egg yolk phosphatidylcholine, soybean phosphatidylcholine, hydrogenated soybean phosphatidylcholine, dilauroyl phosphatidylcholine, dimyristoyl phosphatidylcholine, dioleoyl phosphatidylcholine, dipalmitoylphosphatidylcholine, and distearoylphosphatidylcholine; phosphatidylethanolamines, such as egg yolk phosphatidylethanolamine, soybean phosphatidylethanolamine, dilauroyl phosphatidylethanolamine, dimyristoylphosphatidylethanolamine, dioleoyl phosphatidylethanolamine, dipalmitoyl phosphatidylethanolamine, and distearoyl phosphatidylethanolamine; phosphatidylglycerols, such as egg yolk phosphatidylglycerol, dilauroyl phosphatidylglycerol, dimyristoyl phosphatidylglycerol, dioleoyl phosphatidylglycerol, dipalmitoyl phosphatidylglycerol, and distearoyl phosphatidylglycerol; phosphatidylinositols, such as hydrogenated egg yolk phosphatidylinositol, soybean phosphatidylinositol, dilauroyl phosphatidylinositol, dimyristoyl phosphatidylinositol, dioleoyl phosphatidylinositol, dipalmitoyl phosphatidylinositol, and distearoyl phosphatidylinositol; phosphatidylserines, such as dilauroyl phosphatidylserine, dimyristoyl phosphatidylserine, dioleoyl phosphatidylserine, dipalmitoyl phosphatidylserine, and distearoyl phosphatidylserine; phosphatidic acids, such as dilauroyl phosphatidic acid, dimyristoyl phosphatidic acid, dioleoyl phosphatidic acid, dipalmitoyl phosphatidic acid, and distearoyl phosphatidic acid; cardiolipins, such as tetralauroyl cardiolipin, tetramyristoyl cardiolipin, tetraoleoyl cardiolipin, tetrapalmitoyl cardiolipin, and tetrastearoyl cardiolipin; sphyngomyelins; and their derivatives are cited as phospholipids. Fatty acids, such as lauric acid, myristic acid, oleic acid, pahnitic acid, and stearic acid; aliphatic amines, such a laurylamine, myristylamine, palmitylamine, oleoylamine, stearylamine, dilaurylamine, dimyristylamine, dipalmitylamine, dioleoylamine, and distearylamine; aliphatic alcohols, such as lauryl alcohol, myristyl alcohol, oleoyl alcohol, palmityl alcohol, and stearyl alcohol, and their derivatives and salts are cited as fatty acids.

Ceramide, spyngosine, ganglioside, and their derivatives are cited as glycolipids.

Fatty acid glycerides, for instance, dilauryol glycerol, dimyristoyl glycerol, dioleoyl glycerol, dipalmitoyl glycerol, and distearoyl glycerol are cited as glycerides. Dimyristoyl dimethylammoniumpropane, dioleoyl dimethylammoniumpropane, dipalmitoyl dimethylammoniumpropane, distearoyl dimethylammoniumpropane, and dioleoyloxy dimethylaminopropane hydrochloride; aliphatic trimethylammoniumpropanes, for instance, dimyristoyl trimethylammonium propane, dioleoyl trimethylammonium propane, dipalmitoyl trimethylammoniumpropane, and distearoyl trimethylammonium propane, and their derivatives can be cited as aliphatic dimethylammonium propanes.

Cholesterol and its derivatives are cited as cholesterols.

A variety of methods can be selected for preparation of these colloidal carriers. For instance, a method such as the thin film method, reverse-phase evaporation, lyophilization, spray drying, ethanol introduction, and ether introduction can be selected as the method of preparing liposomes. A method such as ultrasound, French pressing, extrusion, surfactant removal, $Ca^{2+}$ fusion, and freezing and thawing can be selected for the purpose of controlling size, the number of lamellae, internal aqueous phase capacity, and the like. It is also possible to prepare liposomes by mixing the above-mentioned conjugate of a lipid, peptide, and water-soluble polymer with other liposome structural components, and the above-mentioned conjugate of a lipid, peptide, and water-soluble polymer can be introduced by addition to the liposome that has already been prepared. Phospholipids, fatty acids, glycolipids, glycerides, cholesterols, and their derivatives and the like are cited as liposome structural components. One or two or more of these liposome structural components can be added. The content of conjugate of lipid, peptide, and water-soluble polymer to liposome component is within a range of preferably 0.01 to approximately 20% (mol/mol), particularly 0.1 to approximately 15% (mol/mol), ideally approximately 1 to 10% (mol/mol). The particle diameter of the liposomes that have been prepared is preferably within a range of approximately 20 to 800 nm, particularly approximately 20 to approximately 600 nm, ideally approximately 20 to 400 nm.

Moreover, methods such as the thin film method, O/W emulsification, and dialysis can be selected as the micelle preparation method (J. Contrl. Rel., 48, 195, 1997, J. Contrl. Rel., 78, 155, 2002). In addition, it is possible to prepare micelles comprising only the above-mentioned conjugate of a lipid, peptide, and water-soluble polymer, or other additives can be added. The content of the conjugate of a lipid, peptide, and water-soluble polymer to the micelle component is within a range of preferably approximately 20% (mol/mol) or more, particularly approximately 50% (mol/mol) or more. Two or more additives can be added in addition to the conjugate of the lipid, peptide, and water-soluble polymer. The particle diameter of the micelles that are prepared is within a range of preferably approximately 10 to approximately 500 run, particularly approximately 20 to 400 run.

There are no special restrictions to the drug that is used in the present invention as long as it is an active ingredient that is effective therapeutically or an active ingredient that is effective prophylactically. Examples of this pharmaceutical active ingredient are hypnotics and sedatives, sleep aids, anti-anxiety agents, anticonvulsants, antidepressants, anti-Parkinson's agents, psychoneurological agents, CNS drugs, local anesthetics, muscoloskeletal relaxants, autonomic nerve agents, antipyretic analgesic anti-inflammatories, antispasmodics, anti-vertigo agents, cardiotonics, agents for arrhythmia, diuretics, agents for hypertension, vasoconstrictors, vasodilators, drugs for the circulatory system, agents for hyperlipidimeia, agents that promote respiration, antitussives, expectorants, antitussive expectorants, bronchodilators, antidiarrheal agents, agents for controlling intestinal function, agents for peptic ulcers, digestives, antacids, laxatives, cholagogues, gastrointestinal drugs, corticosteroids, hormones, agents for the urinary tract, vitamins, hemostatics, agents for liver disease, agents for the treatment of gout, agents for diabetes, antihistamines, antibiotics, antibacterial agents, anti-malignant tumor agents, chemotherapeutic agents, cold remedies, nutritional supplements, and osteoporosis drugs. Anti-inflammatory, anti-pyretic, antispasmodics or anticonvulsants, such as indomethacin, diclofenac, diclofenac sodium, codeine, ibuprofen, phenylbutazone, oxyphenbutazone, mepirizole, aspirin, ethenzamide, acetaminophen, aminopyrine, phenacetin, butylbromide scopalamine, morphine, etomidrin, pentazocine, fenoprofen calcium, naproxen, celecoxib, valdecoxib, and tramadol; anti-rheumatoid arthritis drugs, such as etodolac; anti-malignant tumor drugs, such as fluorouracil, carmofur, aclarubicin hydrochloride, daunorubicin hydrochloride, doxorubicin hydrochloride, mitomycin, paclitaxel, epirubicin hydrochloride, idarubicin hydrochloride, pirarubicin hydrochloride, belomycin, pepromycin sulfate, etoposide, irinotecan hydrochloride, nogitecan hydrochloride, vinorelbine tartrate, docetaxel, vincristine sulfate, vindesine sulfate, vinplastin sulfate, tamoxifen citrate, shizofiran, krestin, gefitinib, cisplatin, cyclophosphamide, and thiotepa; corticosteroids, such as epinephrine, triamsinolon, hydrocortisone, cortisone acetate, dexamethasone, paramethasone acetate, halopredone acetate, fludorocortisone acetate, norepinephrine, prasterone, prednisolone, and betamethasone; and antibiotics, such as talampicillin hydrochloride, cefotetan, josamycin, tetracycline hydrochloride, doxacycline hydrochloride, and minocycline hydrochloride. Both the free form and and the pharmaceutically acceptable salt of the drug can be used. Moreover, one or a combination of two or more drugs can be used.

The above-mentioned liposome preparation method can be used as the method of preparing liposomes comprising a drug. It is also possible to prepare the liposomes by mixing the drug with other liposome structure component, and it is further possible to encapsulate the drug in the liposomes by adding the drug to pre-prepared liposomes. For instance, liposomes encapsulating a drug can be prepared by mixing a drug and the conjugate of lipid, peptide and water-soluble polymer and other liposome structural components to form a thin film and then performing hydration treatment. Moreover, it is also possible to encapsulate the drug in the liposomes by performing freezing and thawing, the pH gradient method, and the like on pre-prepared liposomes comprising a conjugate of lipid, peptide, and water-soluble polymer. Drug that is not encapsulated in the liposomes can be removed by dialysis, gel filtration, ultracentrifugation, and the like. The content of drug to liposome components is within a range of preferably 0.01 to approximately 70% (w/w), particularly 0.1 to approximately 50% (w/w), ideally approximately 1 to approximately 30% (w/w).

Moreover, it is possible to use the above-mentioned micelle preparation method as the method of preparing micelles comprising a drug. Drug that is not encapsulated in the micelles can be removed by dialysis, gel filtration, ultracentrifugation, and the like. The content of drug to liposome components is within a range of preferably 0.01 to approximately 70% (w/w), particularly 0.1 to approximately 50% (w/w), ideally approximately 1 to approximately 30% (w/w).

(5) Tissue-specific Drug Delivery Systems that use Colloidal Carrier

The tissue-specific drug delivery system used in the present invention means a system with which using a colloidal carrier comprising a drug and a conjugate of a lipid, peptide, and water-soluble polymer, the carrier adheres to the cells of target tissue and releases the drug as a result of the enzyme substrate peptide segment of the above-mentioned conjugate being cleaved in response to enzyme that is specifically secreted from the diseased tissue. Moreover, it means the above-mentioned system that uses a colloidal carrier having the property of adhering to the cells of the target tissue. The drug is incorporated in the colloidal carrier and transported to the target tissue. The adhesion to cells used in the present invention means that the lipid segment of the carrier interacts with the cell membrane, and there are also cases where it means chemical association. Moreover, after adhesion and chemical association, the carrier is taken up inside the cells as a result of fusion with the cell membrane (membrane fusion), and the like, and the drug that has been transported up to the target tissue is released.

Membrane fusion is the phenomenon where two lipid membranes merge to become one membrane and is an important process related to many cell phenomena. Membrane fusion is related to many processes in the cell, including endocytosis and exocytosis, endoplasmic reticulum transport, and the like. Nevertheless, large molecules, such as ions, polar polymers, proteins, genes, and the like, will not pass through the cell membrane. It is reported that in order to effectively transport biologically active substances that realize their activity in cells, a carrier that will introduce these substances to the cytoplasm is necessary, and liposomes having membrane fusibility are capable of transporting substances encapsulated inside the liposomes very efficiently to cytoplasm by fusing with the cell membrane and endosome membrane and therefore are useful as a system for delivery to cytoplasm (*Proc. Natl. Acad. Sci. USA*, 84, 7413, 1987).

Moreover, in addition to the above-mentioned system, the conjugates of the present invention can also be used as means for solubilization of slightly soluble drugs. That is, because the conjugates of the present invention have hydrophilic groups and lipophilic groups within one molecule, when dispersed in water, the hydrophilic groups move toward the outside and the lipophilic groups moves toward the inside to form a small aggregate (micelle) once a certain concentration is reached. Therefore, substances that are slightly soluble in water can be taken up by the micelle to display a solubilizing effect.

The amount of derivative of water-soluble polymer and lipid added in the case of liposomes has an effect on conformation of the water-soluble polymer on the liposome membrane surface, thickness of the hydrate layer, and liposome retention in the blood (*Adv. Drug. Cel. Rev.*, 24, 165, 1997). There is a particularly strong effect on changes in conformation of the water-soluble polymer, and changes in conformation occur with polyethylene glycol having a molecular weight of 2,000 when the amount of derivative of water-soluble polymer and lipid is 4 mol % of the total amount of lipid and with polyethylene glycol having a molecular weight of 5,000 when the amount is 2 mol % of the total amount of lipid (*Biophys. J*, 68, 1903, 1995).

What type of structure the amphipathic substance forms in the case of micelles has a strong effect on the extent of hydrophilicity and lipophilicity. Amphipathic substances having a hydrophilic water-soluble polymer and lipophilic lipid are relatively hydrophilic and will form micelles alone. Moreover, a mixed micelle can be formed by adding approximately 70% of a surfactant to a substance that forms micelles (Nojima et al. (editors), *Liposomes, Nankodo Co., Ltd.*).

PREFERRED EMBODIMENTS OF THE INVENTION

Figure 1:
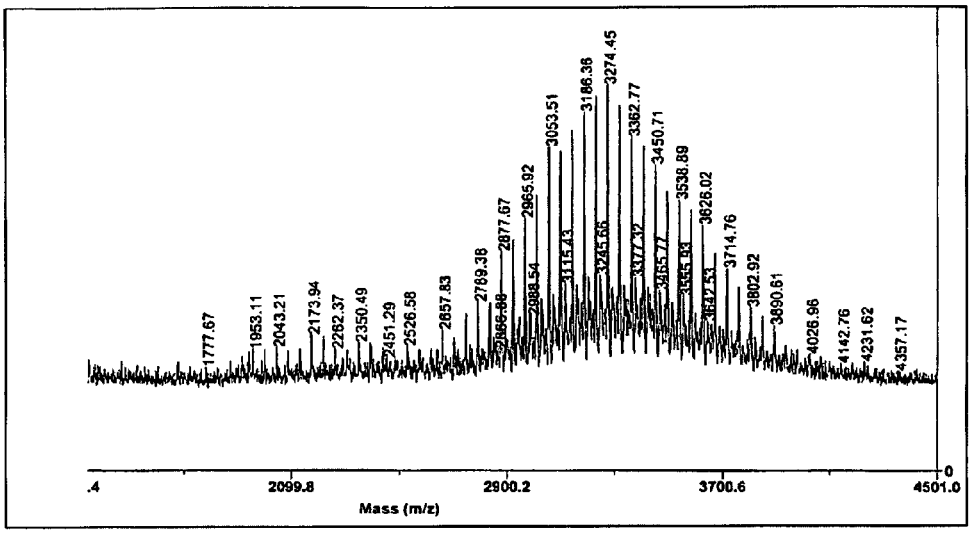
FIG. 1 is the results of MALDI-TOFMS determination of Fmoc-GPQGIAGWG-PEG (SEQ ID NO:22).

The present invention will now be further described with examples, but the present invention is not limited to these examples.

Measurement methods, analysis methods, and so forth

[RP-HPLC Analysis]

Purity and enzyme decomposition were evaluated during synthesis of 9-fluorenylmethylcarbonyl (Fmoc)-glycyl-prolyl-glutamyl-glycyl-isoleucine-alanyl-glycyl-tryptophanyl-glycine (Fmoc-Gly-Pro-Gln-Gly-Ile-Ala-Gly-Trp-Gly; SEQ ID NO:2 1). It should be noted that the 9-fluorenylmethyloxycarbonyl (Fmoc) groups were detected by fluorescence.

The system was the LC10A (Shimadzu Corporation), the column was the TSKGEL ODS-80Ts QA φ=4.6 mm×250 mm (Toso), the mobile phase was 0.1% TFA/CH$_3$CN=65/35, the flow rate was 1.0 ml/min, the detector was a fluorescence spectrophotometer, wavelength was Ex 265 nm, Em 305 nm, and oven temperature was 40° C.

[MALDI-TOF/MS Analysis]

Synthesis of 9-fluorenylmethyloxycarbonyl (Fmoc)-glycyl-prolyl-glutamyl-glycyl-isoleucyl-alanyl-glycyl-tryptophanyl-glycine (Fmoc-Gly-Pro-Gln-Gly-Ile-Ala-Gly-Trp-Gly; SEQ ID NO:21), 9-fluorenylmethyloxycarbonyl (Fmoc)-glycyl-prolyl-glutamyl-glycyl-isoleucyl-alanyl-glycyl-tryptophanyl-glycyl (Fmoc-Gly-Pro-Gln-Gly-Ile-Ala-Gly-Trp-Gly)-amidopropyl polyoxyethylene methyl ether (SEQ ID NO:22), and distearoyl phosphatidylethanolamine-glutaryl-Gly-Pro-Gln-Gly-Ile-Ala-Gly-Trp-Gly-amidopropyl polyoxyethylene methyl ether (SEQ ID NO:23) was confirmed.

A small amount of each sample was dissolved in CHCl$_3$/MeOH mixture and mixed with matrix (2,5-dihydroxybenzoic acid) solution (in CH$_3$CN) and dried. Measurement was performed with the Voyager Elite XL (Applied Biosystems).

[TLC Analysis]

Progression of the reaction was monitored and the product was identified. The sample was spotted on a thin layer plate (Merck Silicagel 60) and developed with CH$_3$Cl/MeOH/H$_2$O=65/25/4 (v/v). Detection was performed by fluorescence detection, ninhydrin detection, or I$_2$ vapor [detection].

[$^1$H-NMR Analysis]

Synthesis of distearoyl phosphatidylethanolamine-glutamyl-glycyl-prolyl-glutamyl-glycyl-isoleucyl-alanyl-glycyl-tryptophanyl-glycyl (DSPE-Gly-Pro-Gln-Gly-Ile-Ala-Gly-Trp-Gly) amidopropyl polyoxyethylene methyl ether (SEQ ID NO:23) was confirmed. The sample was dissolved in heavy water and then determinations were performed with the JNM-AL400 (JEOL, Ltd.).

[Gel Permeation Determination Method]

Evaluation of enzymatic degradation of 9-fluorenylmethyloxycarbonyl (Fmoc)-glycyl-prolyl-glutamyl-glycyl-isoleucyl-alanyl-glycyl -tryptophanyl-glycyl (Fmoc-Gly-Pro-Gln-Gly-Ile-Ala-Gly-Trp-Gly) amidopropyl polyoxyethylene methyl ether (SEQ ID NO:22) was performed.

After mixing in 0.5 ml of sample in 0.5 ml of acetonitrile, the mixture was filtered and gel filtration was performed. The system was the LC-10A (Shimadzu Corporation), the column was the Superdex peptide HR10/30 (Amersham-Pharmacia-Biotech), the mobile phase was 10 mM HEPES/150 mM NaCl, pH 7.4, flow rate was 1.0 ml/min, the detector was a fluorescence spectrophotometer, and wavelength was Ex 265 nm, Em 305 nm.

[Polyethylene Glycol Quantitative Determination]

Quantitative determination of the polyethylene glycol incorporated into the liposome was performed by the picric acid method (Int. J. Pharm., 203, 255, 2000).

[Choline Quantitative Determination Method]

Quantitative determination of phosphatidyl choline comprising the liposomes was performed with the Phospholipid C-Test Wako (Wako Pure Chemical Industries, Ltd.).

[Particle Diameter Determination]

The particle diameter of the micelles and the liposomes was determined with the NICOMP Model 370 (Particle Sizing Systems, Inc.).

[Zeta Potential Measurement Method]

Zeta potential of the liposomes was measured using the Zetasizer 3000HSA (Malvern Instruments).

[Cholesteryl anthracene-9-carboxylate (CA) assay]

Assay of cholesteryl anthracene-9-carboxylate in liposomes, plasma, and cancer tissue was conducted by RP-HPLC (Journal of Chromatography, A, 421, 43, 1987).

1. Gly-Pro-Gln-Gly-Ile-Ala-Gly-Trp-Gly peptide 1.1. Synthesis of 9-fluorenylmethyloxycarbonyl (Fmoc)-glycyl-prolyl-glutamyl-glycyl-isoleucyl-alanyl-glycyl -tryptophanyl-glycine (Fmoc-Gly-Pro-Gln-Gly-Ile-Ala-Gly-Trp-Gly) (Fmoc-GPQGIAGWG; SEQ ID NO:2 1)

Fmoc removal was performed by adding 20% piperidine/dimethylformamide to Fmoc-Gly-Wang Resin. Dimethylformamide was added and the resin was washed. Then amino acids, 2-(1H-benzotriazole-1-yl)-1,1,3,3-tetramethyluronium hexafluorophosphate (HBTU), N,N-diisopropylethylamine (DIEA), and dimethylformamide were added to couple the amino acids to the amino acid residues bound to the resin. Dimethylformamide was added and the resin was washed. The procedure of removal of Fmoc, washing, coupling and washing was repeated until the amino acids of the entire sequence had been coupled. Then trifluoroacetic acid was added and the peptide was cleaved from the resin. The marked compound was obtained by reprecipitating the peptide with ether and purifying the crude product that was obtained.

Confirmation of the product was performed by RP-HPLC analysis and MALDI-TOFMS analysis. When purity of the Fmoc-GPQGIAGWG (SEQ ID NO:21) was calculated from the peak area ratio as a result of RP-HPLC measurement, purity of 99.5% was confirmed. Moreover, signals were observed at 1,087 Da and 1,103 Da as a result of MALDI-TOFMS. Theoretical molecular weight of the Fmoc-GPQGIAGWG (SEQ ID NO:21) was 1,063.5 Da, but theoretical molecular weight of the Na adduct and K adduct was 1,086.5 Da and 1,102.6 Da. Therefore, the determinations that were obtained were of the Na adduct and K adduct. The molecular weights were determined in the same way as the theoretical values, indicating that Fmoc-GPQGIAGWG (SEQ ID NO:21) had been synthesized.

1.2. Synthesis of 9-fluorenylmethyloxycarbonyl (Fmoc)-glycyl-prolyl-glutamyl-glycyl-isoleucyl-alanyl-glycyl -tryptophanyl-glycyl (Fmoc-Gly-Pro-Gln-Gly-Ile-Ala-Gly-Trp-Gly)-amidopropyl polyoxyethylene methyl ether (Fmoc-GPQGIAGWG-PEG; SEQ ID NO:22)

One-hundred milligrams of Fmoc-GPQGIAGWG (SEQ ID NO:21) were dissolved by adding 5 ml of N,N-dimethylformamide, 11.9 mg of N-hydroxysuccinimide were added, 38.5 mg of dicyclohexylcarbodiimide were further added, and the mixture was stirred for two hours at room temperature. Then a solution of 187 mg of methoxypolyethylene glycol-propylamine (Sunbrite MEPA-20H, NOF Corporation) dissolved in 2.3 ml of N,N-dimethylformamide were added and reacted for 18 hours at 45° C. After the reaction, the reaction liquid was cooled to 0° C. or lower and filtered to remove the insoluble matter. Then it was rinsed with 5 ml of chloroform. This filtrate was passed through a strongly acidic cation exchange resin (Daiyaion SK-1, Mitsubishi Chemical Corporation) column and the unreacted methoxypolyethylene glycol-propylamine was removed. Then it was desiccated under reduced pressure in an evaporator. Twenty milliliters of ethyl acetate were added and the product was cooled to 0° C. or lower and filtered to obtain crude crystals. Five milliliters of water for injection were added to remove the impurities. Lyophilization was performed to obtain 157 mg of marked compound.

Progression of the reaction was monitored and the product was identified by thin-layer chromatography (TLC) using a silica gel plate. The substance was qualitative analyzed by coloration with iodine vapor and comparison with the marked substance using a mixed solvent of chloroform, methanol, and water at a mixture ratio (volume ratio) of 65:25:4. The end point of the reaction was confirmed based on shifting of the spots of methoxypolyethylene glycol-propylamine, which are detected near an Rf of 0.6, and of Fmoc-GPQGIAGWG (SEQ ID NO:21), which are detected near an Rf of 0.2, to spots detected near an Rf of 0.75 by the above-mentioned TLC. Confirmation of the product was based on the presence of monomethoxyoxyethylene chains and peptide chains by detection of the methyl group of the terminal methoxy group δ: near 3.4 ppm of the terminal end methoxy and the ethylene group δ: near 3.5 ppm of polyoxyethylene derived from methoxypolyethylene glycol-propylamine and the methylene group δ: near 1.5 ppm derived from the peptide using ¹H-NMR. When MALDI-TOFMS measurement was performed after purification of this substance, a signal derived from PEG was observed virtually in the middle at 3,274 Da (FIG. 1). The calculated molecular weight of the Fmoc-GPQGIAGWG-PEG (SEQ ID NO:22) was 3,250 Da with the degree of polymerization of the PEG n=48 and virtually coincided [with the molecular weight from MALDI-TOFMS]. This apparently is observed as the Na adduct=+23 Da. Therefore, it could be confirmed that Fmoc-GPQGIAGWG-PEG (SEQ ID NO:22) had been synthesized.

1.3. Synthesis of H₂N-Gly-Pro-Gln-Gly-Ile-Ala-Gly-Trp-Gly-amidopropyl Polyoxyethylene Methyl Ether (GPQ-GIAGWG-PEG; SEQ ID NO:24)

First, 145 mg of the Fmoc-GPQGIAGWG-PEG (SEQ ID NO:22) obtained above were dissolved in 3 ml of N,N-dimethylformamide, 1 ml of piperidine was added, and a reaction was performed by stirring for 40 minutes at room temperature. The reaction liquid was desiccated under reduced pressure with an evaporator. Then 10 ml of ethyl acetate were added and the mixture was cooled to 0° C. or lower and filtered to obtain crude crystals. This purification process was repeated another two times to obtain 67 mg of the marked compound. Progression of the reaction was monitored and the product was identified by the same TLC as described above. The reaction end point was confirmed based on shifting of the spot of Fmoc-GPQGIAGWG-PEG (SEQ ID NO:22), which is detected near an Rf of 0.75, to near an Rf of 0.5 and further, by ninhydrin coloration of the spot.

1.4. Synthesis of Distearoyl Phosphatidylethanolamine Glutarate (DSPE-Glt)

Ten milliliters of chloroform were added to 748 mg distearoyl phosphatidylethanolamine and stirred at 40° C., 100 mg of sodium acetate and 170 mg of glutaric anhydride were added and the reaction was performed for 5 hours at 50° C. The reaction end point was confirmed by the same TLC as described above, and as the point where there was no distearoyl phosphatidylethanolamine by ninhydrin coloration. The reaction liquid was cooled and then 10 ml of acetone were added to obtain crude crystals. Twenty milliliters of 2-propranolol were added and the product was cooled and filtered to obtain 705 mg of the marked compound.

1.5. Synthesis of Distearoyl Phosphatidylethanolamine-glutaryl-Gly-Pro-Gln-Gly-Ile-Ala-Gly-Trp-Gly-amidopropyl Polyoxyethylene Methyl Ether (DSPE-GPQGIAGWG-PEG; SEQ ID NO:23)

First, 34 mg of the DSPE-Glt obtained above were dissolved in 0.3 ml of chloroform, 5.3 mg of N-hydroxysuccinimide and 16.5 mg of dicyclohexylcarbodiimide were added and stirred for two hours at room temperature. The reaction liquid was filtered to remove the insoluble matter and obtain distearoyl phosphatidylethanolamine glutaryl succinimide solution. Sixty milligrams of the GPWGLAGWG-PEG (SEQ ID NO:24) obtained above were dissolved in 3 ml of chloroform, the distearoyl phosphatidylethanolamine glutaryl succinimide solution was added, and the mixture was stirred and reacted for five hours at 40° C. After the reaction, the product was filtered to remove the insoluble matter. Ten milliliters of ethyl acetate and 5 ml of hexane were added to this solution. After cooling, the mixture was filtered to obtain crude crystals. Purification was performed by repeating twice the crystallization process whereby 2 ml of ethyl acetate were added to the crude crystals and the mixture was cooled and filtered to obtain crystals. Forty-five milligrams of the marked compound were obtained.

Figure 3:
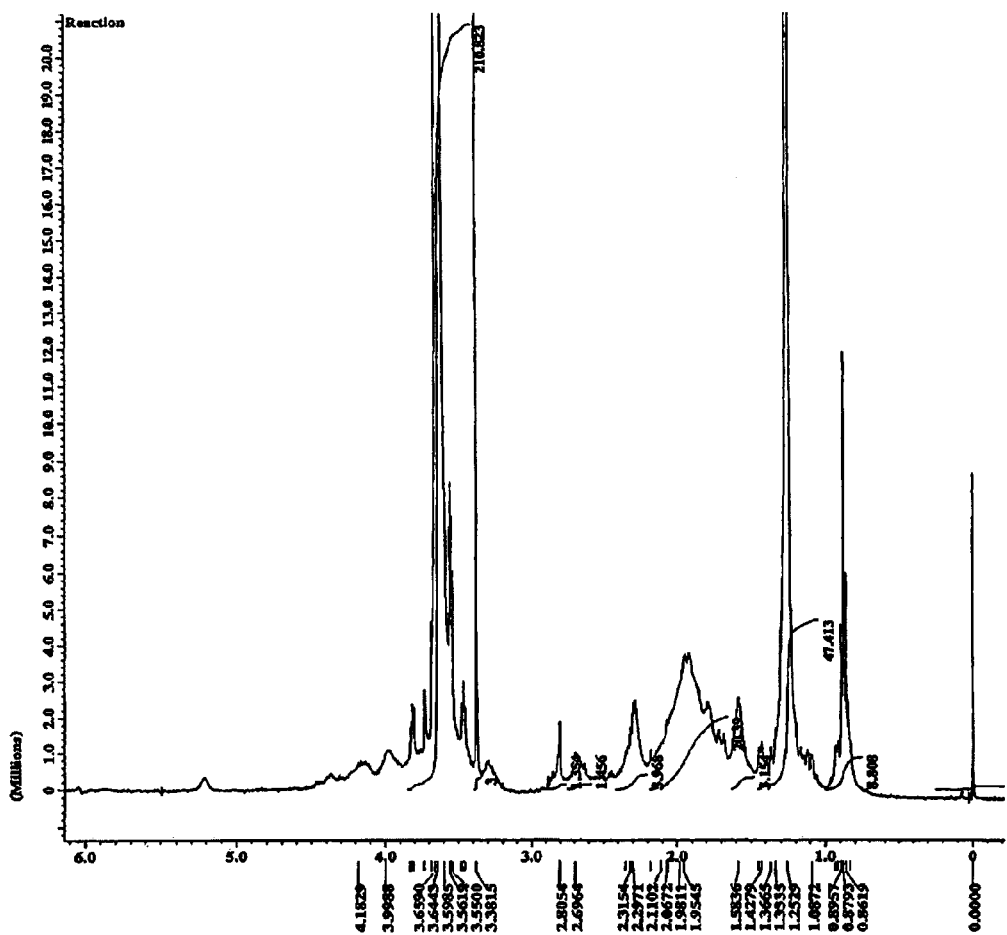
FIG. 3 is the results of $^1$H-NMR determination of DSPE-GPQGIAGWG-PEG (SEQ ID NO:23).

Progression of the reaction was monitored and the product was identified by the same TLC as described above. Confirmation was based on the fact that the spot of GPQ-GIAGWG-PEG (SEO ID NO:24), which is detected near an Rf of 0.5, and the spot of DSPE-Glt, which is detected near an Rf of 0.3, had shifted to spots detected near an Rf of 0.8. The product was confirmed by the presence of monomethoxyoxyethylene chains, peptide chains, and distearoyl phosphatidylethanol amine based on detection of the methyl group of the terminal end methoxy δ: near 3.4 ppm and the polyoxyethylene group δ: near 3.5 ppm derived from methoxypolyethylene glycol-propylamine, detection of δ: near 1.5 ppm derived from peptide, and further, detection of the terminal methyl group of the acyl group δ: near 0.9 ppm derived from distearoyl phosphatidylethanolamine (FIG. 3).

Figure 2:
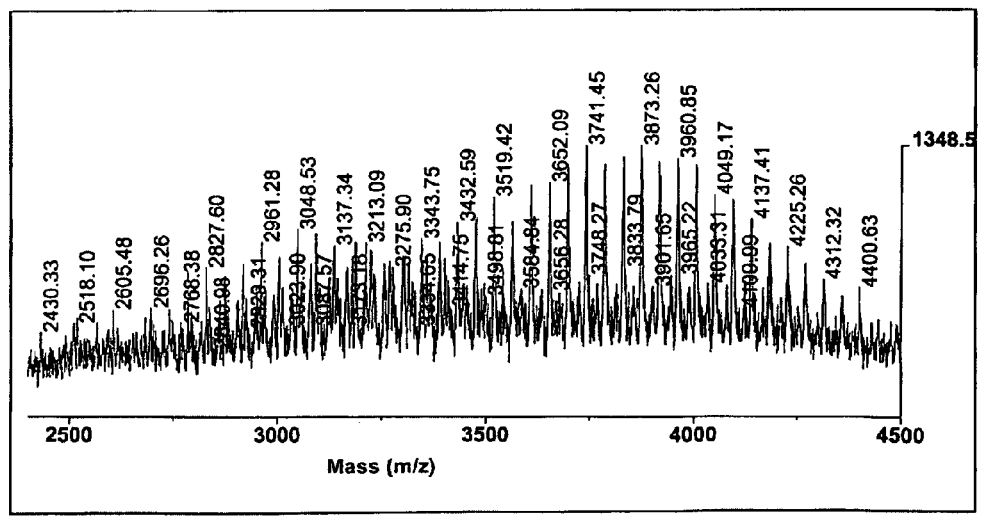
FIG. 2 is the results of MALDI-TOFMS determination of DSPE-GPQGIAGWG-PEG (SEQ ID NO:23).

When this sample was analyzed by MALDI-TOFMS, a signal derived from PEG was observed at virtually the middle value of 3,873 D (FIG. 2). The calculated molecular weight of DSPE-GPQGIAGWG-PEG (SEQ ID NO:23) was 3,872 Da with the degree of polymerization of PEG n=48, which virtually coincides with the actual measurement.

1.6. Enzymatic Degradation of Peptide and Peptide-PEG (1) Studies of Enzymatic Degradation of Fmoc-GPQ-GIAGWG (SEQ ID NO:21)

In order to confirm specificity of Fmoc-GPQGIAGWG (SEQ ID NO:2 1) as an enzyme substrate, enzymatic degradation by MMP-2, collagenase, carboxypeptidase A, aminopeptidase-1, and trypsin were studied.

Fmoc-GPQGIAGWG (SEQ ID NO:21) was dissolved in Tris buffer (100 mM Tris/100 mM NaCl/10 mM CaCl₂/0.05% BRIJ35, pH 7.5) and adjusted to a pre-determined concentration. MMP-2, collagenase, carboxypeptidase A, aminopeptidase-1, and trypsin were each diluted or dissolved in Tris buffer. Each enzyme solution was added to Fmoc-GPQGIAGWG (SEQ ID NO:21) solution that had been heated to 37° C. and incubated for a pre-determined time at 37° C. The final concentration of the enzymes was as shown below: MMP-2: 0.17 µg/ml, collagenase:7 µg/ml, carboxypeptidase A:10 µg/ml, aminopeptidase-1:10 µg/ml, trypsin:10 µg/ml. After a pre-determined time, the same amount of acetonitrile was added to the sample solutions and they were filtered with a 0.5 µm filter (Millex-LH MILIPORE). The FMOC GPQGIAGWG Fmoc-GPQGIAGWG (SEQ ID NO:2 1) in the filtrate was separated and quantitatively determined by RP-HPLC.

When the unit weight of each enzyme at the beginning (15 minutes) of the enzymatic degradation reaction and the degradation rate of the Fmoc-GPQGIAGWG (SEQ ID NO:21) per unit time were compared, the degradation rate of Fmoc-GPQGIAGWG (SEQ ID NO:21) by MMP-2 was 26.9x, 38.8 x, and 14.2x that of collagenase, carboxypeptidase A, and aminopeptidase-1, respectively. Degradation of Fmoc-GPQGIAGWG (SEQ ID NO:21) by trypsin was not observed.

The results of this study confirm that enzymatic degradation of Fmoc-GPQGIAGWG (SEQ ID NO:21) by collagenase, carboxypeptidase A, and aminopeptidase-1 is low and that MMP-2 has high specificity for this conjugate.

(2) Studies of Degradation of Fmoc-GPQGIAGWG-PEG (SEQ ID NO:22) by MMP-2

The effects on degradation by MMP-2 when PEG bonded with Fmoc-GPQGIAGWG (SEQ ID NO:21) were evaluated.

Fmoc-GPQGIAGWG-PEG (SEQ ID NO:22) was dissolved in Tris buffer (100 mM Tris/100 mM NaCl/10 mM $CaCl_2$/0.05% BRIJ35, pH of 7.5) and adjusted to a pre-determined concentration. MMP-2 solution was diluted with Tris buffer. The MMP-2 solution was added to the Fmoc-GPQGIAGWG-PEG (SEQ ID NO:22) solution that had been heated to 37° C. and incubated for a pre-determined time at 37° C. The final concentration of MMP-2 was 0.34 µg/ml. After a pre-determined time, the same amount of acetonitrile was added to the sample solution and the mixture was filtered with a 0.5 µm filter (Millex-LH MILIPORE). The Fmoc-GPQGIAGWG-PEG (SEQ ID NO:22) in the filtrate was separated and quantitatively determined by gel filtration.

Figure 4:
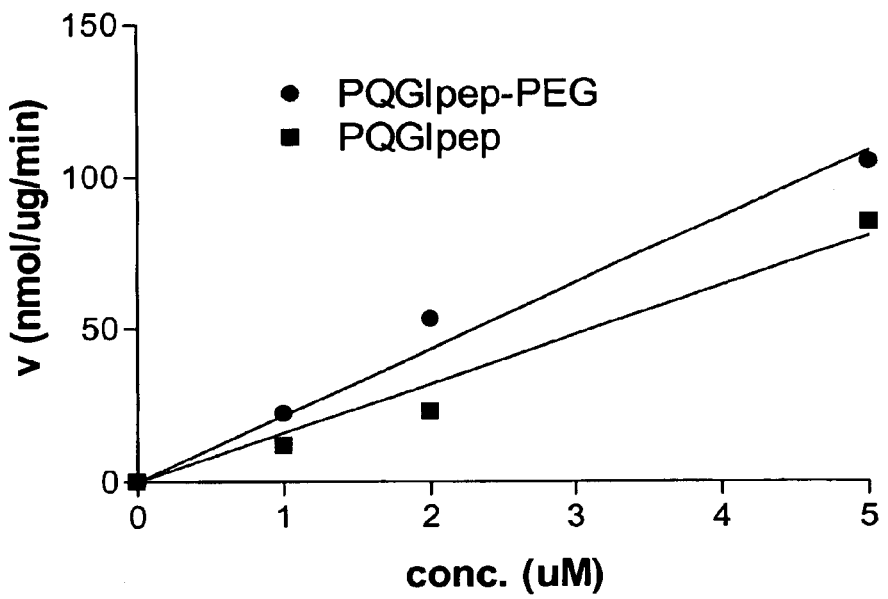
FIG. 4 is the results of enzymatic degradation studies

When the unit weight of MMP-2 at the beginning of the enzymatic degradation reaction (15 minutes) and the degradation rate of Fmoc-GPQGIAGWG (SEQ ID NO:22) and Fmoc-GPQGIAGWG-PEG (SEQ ID NO:22) per unit time were compared, it was confirmed that they are virtually the same (FIG. 4). Therefore, it was confirmed that there is virtually no effect on degradation by an enzyme when an enzyme substrate peptide is modified by PEG.

1.7. Method of Peptide-PEG Micelle Preparation

Fmoc-GPQGIAGWG-PEG (SEQ ID NO:22) was dissolved in Tris buffer (100 mM Tris/100 mM NaCl/10 mM $CaCl_2$/0.05% BRIJ35, pH of 7.5) and adjusted to a pre-determined concentration. Then particle diameter was determined by a laser diffraction particle diameter distribution determination device (NICOMP Model 370)(Table1).

It was ascertained that an aggregate having a particle diameter of approximately 200 nm forms at 5 µm or more of Fmoc-GPQGIAGWG-PEG (SEQ ID NO:22). Moreover, the laser scattering intensity during NICOMP determination showed concentration dependency and it was impossible to determine the particle diameter at 2 µM or less. Therefore, it was concluded that the critical micelle concentration is near 5 µM.

TABLE 1

Determination of Fmoc-PQGIpep-PEG particle diameter

| Concentration (µM) | 1 | 2 | 5 | 10 | 20 | 50 | 100 |
|---|---|---|---|---|---|---|---|
| Particle diameter (nm) | nd | nd | 232 | 200 | 205 | 210 | 237 |
| s.d. (%) | — | — | 38.4 | 63.3 | 62.3 | 53.2 | 39.3 |

1.8. Method of Preparing Liposomes Comprising Lipid-peptide-PEG Conjugates

After a lipid membrane was prepared by adding 2.5, 5.0, and 7.5 mol % of DSPE-GPQGJAGWG-PEG (SEQ ID NO:23) to DPPC/cholesterol, hydration was performed with HEPES buffer (100 mM HEPES/150 mM NaCL, pH of 7.4) containing calcein and liposomes with a particle diameter of approximately 100 nm was prepared by extrusion using a polycarbonate film. In order to remove the DSPE-GPQGIAGWG-PEG (SEQ ID NO:23) and calcein that had not been introduced to the liposomes, the liposomes were dispersed in HEPES buffer and treated by ultra centrifugation (40,000 rpm, 5 h) twice. Quantitative determination of PEG was by the picric acid method, quantitative determination of DPPC was by choline quantitative determination, and quantitative determination of the calcein was by fluorescence determination. The properties of the liposomes were evaluated.

Average particle diameter of the liposomes that were prepared was approximately 120 nm. Moreover, encapsulation of the calcein, which is a water-soluble marker, could be confirmed. Therefore, it was confirmed that liposomes to which DSPE-GPQGIAGWG-PEG (SEQ ID NO:23) are introduced can be prepared.

1.9 Blood Retention and Cancer Tissue Accumulation Studies of DSPE-GPOGIAGWG-PEG (SEQ ID NO:23)-introduced Liposomes (1) Method of Preparing Lipid-peptide-PEG-containing Liposomes and PEG-DSPE-containing Liposomes After preparing lipid membranes by adding 7.5 and 5.0 mol % of DSPE-GPQGIAGWG-PEG (SEQ ID NO:23) and PEG-DSPE, respectively, to DPPC/cholesterol/CA, hydration was performed by HEPES buffer (10 mM HEPES/150 mM NaCl, pH of 7.4) and liposomes were prepared by extrusion using polycarbonate film with a pore diameter of 100 nm. The average particle diameter of the DSPE-GPQGIAGWG-PEG (SEQ ID NO:23)-containing liposomes was approximately 142 nm, and zeta potential was −10.1 mV. The average particle diameter of the PEG-DSPE-containing liposomes was approximately 131 nm, and zeta potential was −15.7 mV.

(2) Mouse Administration Studies (2-1) Plasma Retention Evaluation

Figure 5:
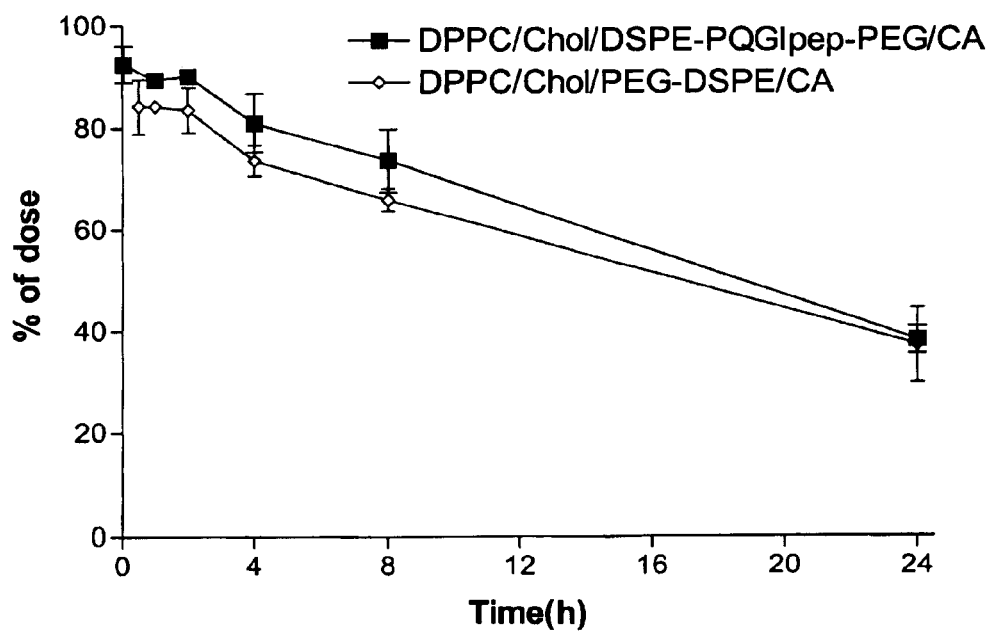
FIG. 5 is the results of measuring changes in the plasma concentration of DSPE-GPQGIAGWG-PEG (SEQ ID NO:23)-containing liposomes and PEG-DSPE-containing liposomes.

The liposomes that were prepared were administered to BALB/c mice (20–25 g) through a caudal vein at a lipid concentration of 25 mg/ml. Blood retention of the liposomes was evaluated by measuring the plasma cholesteryl anthracene-9-carboxylate concentration after a pre-determined time. The changes in the plasma concentration of liposomes are shown in FIG. 5 and the PK parameters are shown in Table 2. It was clear from these results that the DSPE-GPQGIAGWG-PEG (SEQ ID NO:23)-containing liposomes show the same plasma retention as PEG-DSPE-containing liposomes.

TABLE 2

Liposome PK parameters

| PEG conjugate | PK parameter | | |
|---|---|---|---|
| | t 1/2 (h) | Vz (ml/kg) | Cl (ml/h) |
| DSPE-PQGIpep-PEG | 18.0 | 47.2 | 0.039 |
| PEG-DSPE | 19.4 | 52.6 | 0.041 |

(2-2) Accumulation in Cancer Tissue

Figure 6:
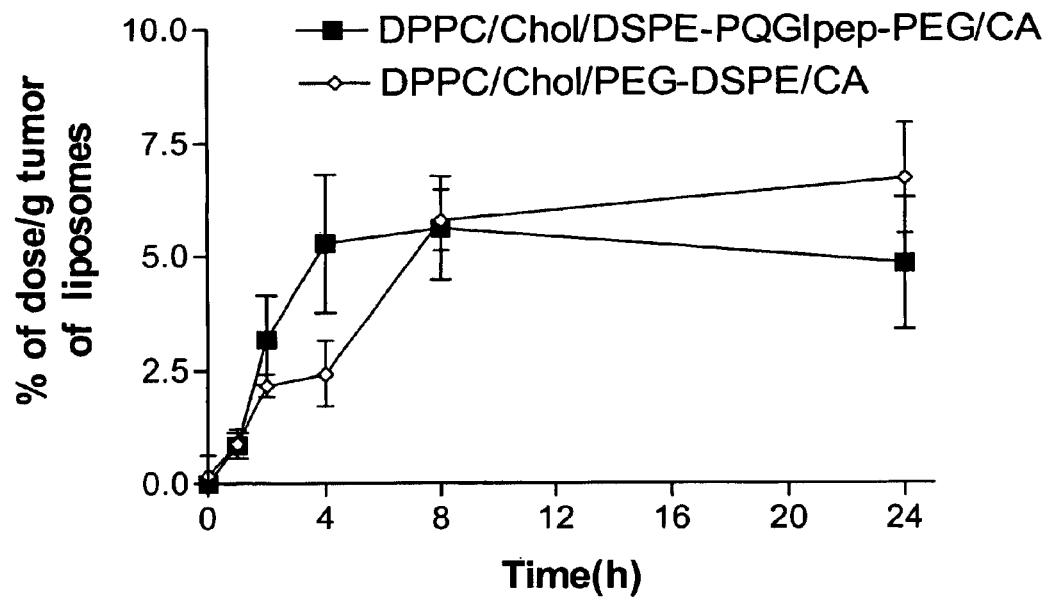
FIG. 6 is the results of measuring cancer tissue accumulation of DSPE-GPQGIAGWG-PEG (SEQ ID NO:23)-containing liposomes and PEG-DSPE-containing liposomes.

Tumor-carrying mice were made by transplanting HT1080 cells subcutaneously in the back region of BALB/c nu/nu mice (20–25 g) at $3 \times 10^6$ cells/100 µL. After rearing the mice for a specific time, the liposomes that had been prepared were administered through a caudal vein at a lipid concentration of 25 mg/ml. After a pre-determined amount of time, cancer tissue was removed and homogenized and the cholesteryl anthracene-9-carboxylate concentration was measured to evaluate liposome accumulation in cancer tissue. Liposome accumulation in cancer tissue is shown in FIG. 6. It was clear from the results that were obtained that the DSPE-GPQGIAGWG-PEG-containing liposomes showed the same cancer tissue accumulation as the PEG-DSPE-containing liposomes.

(3) Desorption of PEG Chain by MMP-2

(3-1) Method of Preparing Lipid-peptide-PEG-containing Liposomes

After preparing a lipid membrane of DPPC/cholesterol/DPPG, hydration was performed with an HEPES buffer (100 mM HEPES/150 mM NaCl, pH of 7.4) and liposomes were prepared by extrusion using polycarbonate film with a pore diameter of 100 nm. An aqueous DSPE-GPQGIAGWG-PEG (SEQ ID NO:23) solution was added to the liposome suspension to 1.0, 2.5, and 5.0 mol % and incubated for one hour at 60° C. to introduce DSPE-GPQGIAGWG-PEG (SEQ ID NO:23) to the liposome surface. The DSPE-GPQGIAGWG-PEG (SEQ ID NO:23) that had not been introduced to the liposome was removed by dispersion in Tris buffer (100 mM Tris/5 mM $CaCl_2$/0.1% bovine serum albumin, pH of 7.5) and ultra-centrifugation (40,000 rpm, 5 h) twice.

(3-2) Studies of PEG Desorption by MMP-2

Figure 7:
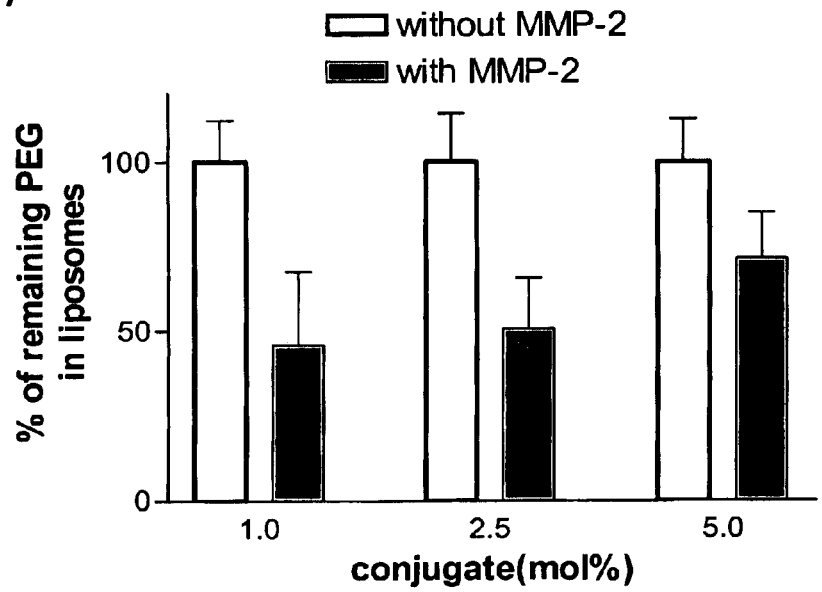
FIG. 7 is the results of studies of PEG desorption from the liposome surface with the addition of MMP-2.

Liposomes were prepared to a liposome lipid concentration of 4 mg/ml and MMP-2 concentration of 1.7 µg/ml using Tris buffer (100 mM Tris/5 mM $CaCl_2$/0.1% bovine serum albumin, pH of 7.5). After incubation for a predetermined time at 37° C., ultracentrifugation (40,000 rpm, 5 h) was performed twice in order to remove the PEG chain. Choline assay and PEG assay of the liposomes were performed. As shown in FIG. 7, desorption of the PEG chain from the liposome surface with the addition of MMP-2 was seen.

2. Gly-Pro-Leu-Gly-Ile-Ala-Gly-Gln-Gly (SEQ ID NO:17) peptide (MMP substrate)

2.1. Synthesis of 9-fluorenylmethyloxycarbonyl (Fmoc)-glycyl-prolyl-leucyl-glycyl-isoleucyl-alanyl-glycyl-glutamyl-glycine (Fmoc-Gly-Pro-Leu-Gly-Ile-Ala-Gly-Gln-Gly) (Fmoc-GPLGIAGQG: SEQ ID NO:25)

Fmoc removal was performed by adding 20% piperidine/dimethylformamide to Fmoc-Gly-Wang Resin. Dimethylformamide was added and the resin was washed. Then amino acids, 2-(1H-benzotriazol-1-yl)-1,1,3,3-tetramethyluronium hexafluorophosphate (HBTU), N,N-diisopropylethylamine (DIEA), and dimethylformamide were added to couple the amino acids to the amino acid residues bound to the resin. Dimethylformamide was added and the resin was washed. The procedure of removal of Fmoc, washing, coupling and washing was repeated until the amino acids of the entire sequence had been coupled. Then trifluoroacetic acid was added and stirred and the peptide was cut from the resin. The title compound was obtained by re-precipitating the peptide with ether and purifying the crude [product] that was obtained.

Confirmation of the product was performed by RP-HPLC analysis and MALDI-TOFMS analysis. When purity of the Fmoc-GPLGIAGQG (SEQ ID NO:25) was calculated from the peak surface area ratio as a result of RP-HPLC determination, purity of 98.7% was confirmed. Moreover, signals were observed at 991 Da as a result of MALDI-TOFMS. Theoretical molecular weight was obtained, indicating that Fmoc-GPLGIAGQG (SEQ ID NO:25) had been synthesized.

2.2. Synthesis of 9-fluorenylmethyloxycarbonyl (Fmoc)-glycyl-prolyl-leucyl-glycyl-isoleucyl-alanyl-glycyl-glutamyl-glycine (Fmoc-Gly-Pro-Leu-Gly-Ile-Ala-Gly-Gln-Gly)-amidopropyl Polyoxyethylene Methyl Ether (Fmoc-GPLGIAGQG-PEG; SEQ ID NO:25)

One-hundred milligrams of Fmoc-GPLGIAGQG (SEQ ID NO:25) were dissolved by adding 5 ml of N,N-dimethylformamide, 11.1 mg of N-hydroxysuccinimide were added, 35.9 mg of dicyclohexylcarbodiimide were further added, and the mixture was stirred for two hours at room temperature. Then a solution of 174 mg of methoxypolyethylene glycol-propylamine (SUNBRITE MEPA-20H, NOF Corporation) dissolved in 2.3 ml of N,N-dimethylformamide were added and reacted for 18 hours at 45° C. After the reaction, the reaction liquid was cooled to 0° C. or lower and filtered to remove the insoluble matter. Then it was rinsed with 5 ml of chloroform. This filtrate was passed through a strongly acidic cation exchange resin (DIAION SK-1, Mitsubishi Chemical Corporation) column and the unreacted methoxypolyethylene glycol-propylamine was removed. Then it was desiccated under reduced pressure in an evaporator. Twenty milliliters of ethyl acetate were added and the product was cooled to 0° C. or lower and filtered to obtain crude crystals. Five milliliters of water for injection were added to remove the impurities. Lyophilization was performed to obtain 146 mg of the title compound.

Progression of the reaction was monitored and the product was identified by thin-layer chromatography (TLC) using a silica gel plate. The substance was submitted to qualitative analysis by coloration with iodine vapor and comparison with the title substance using a mixed solvent of chloroform, methanol, and water at a mixture ratio (volume ratio) of 65:25:4. The end point of the reaction was confirmed based on shifting of the spots of methoxypolyethylene glycol-propylamine, which are detected near an Rf of 0.55, and of Fmoc-GPLGIAGQG-PEG (SEQ ID NO:26), which are detected near an Rf of 0.22, to spots detected near an Rf of 0.63 by the above-mentioned TLC.

2.3. Synthesis of $H_2N$-Gly-Pro-Leu-Gly-Ile-Ala-Gly-Gln-Gly-amidopropyl Polyoxyethylene Methyl Ether (GPLGIAGQG-PEG: SEQ ID NO:27)

First, 140 mg of the Fmoc-GPLGIAGQG-PEG (SEQ ID NO:26) obtained above were dissolved in 3 ml of N,N-dimethylformamide, 1 ml of piperidine was added, and a reaction was performed by stirring for 40 minutes at room temperature. The reaction liquid was desiccated under reduced pressure with an evaporator. Then 10 ml of ethyl acetate were added and the mixture was cooled to 0° C. or lower and filtered to obtain crude crystals. This purification process was repeated two more times to obtain 65 mg of the title compound. Progression of the reaction was monitored and the product was identified by the same TLC as described above. The reaction end point was confirmed based on shifting of the spot of Fmoc-GPLGIAGQG-PEG (SEQ ID NO:26), which is detected near an Rf of 0.66, to near an Rf of 0.32 and further, by ninhydrin coloration of the spot.

2.4. Synthesis of Distearoyl Phosphatidylethanolamine-glutaryl-Gly-Pro-Leu-Gly-Ile-Ala-Gly-Gln-Gly-amidopropyl Polyoxyethylene Methyl Ether (DSPE-GPLGIAGQG-PEG: SEQ ID NO:28)

First, 34 mg of the DSPE-Glt obtained above were dissolved in 0.3 ml of chloroform, and then 5.3 mg of N-hydroxysuccinimide and 16.5 mg of dicyclohexylcarbodiimide were added and stirred for two hours at room temperature. The reaction liquid was filtered to remove the insoluble matter and obtain distearoyl phosphatidylethanolamine glutaryl succinimide solution.

Sixty milligrams of the GPLGIAGQG-PEG (SEQ ID NO:27) obtained above were dissolved in 3 ml of chloroform, the distearoyl phosphatidylethanolamine glutaryl succinimide solution was added, and the mixture was stirred and reacted for five hours at 40° C. After the reaction, the product was filtered to remove the insoluble matter. Ten milliliters of ethyl acetate and 5 ml of hexane were added to this solution. After cooling, the mixture was filtered to obtain crude crystals. Purification was performed by repeating twice the crystallization process whereby 2 ml of ethyl acetate were added to the crude crystals and the mixture was cooled and filtered to obtain crystals. Forty-six milligrams of the title compound were obtained.

Progression of the reaction was monitored and the product was identified by the same TLC as described above. Confirmation was based on the fact that the spot of GPLGIAGQG-PEG (SEQ ID NO:27), which is detected near an Rf of 0.26, and the spot of DSPE-Glt, which is detected near an Rf of 0.15, had shifted to spots detected near an Rf of 0.51. The product was confirmed by the presence of monomethoxyoxyethylene chains, peptide chains, and distearoyl phosphatidylethanol amine based on detection of the methyl group of the terminal end methoxy δ: near 3.4 ppm and the polyoxyethylene group δ: near 3.5 ppm derived from methoxypolyethylene glycol-propylamine, detection of δ: near 1.5 ppm derived from peptide, and further, detection of the terminal methyl group of the acyl group δ: near 0.9 ppm derived from distearoyl phosphatidylethanolamine by $^1$H-NMR.

When this sample was analyzed by MALDI-TOFMS, a signal derived from PEG was observed at virtually the middle value of 3,797 Da (FIG. 2). The calculated molecular weight of DSPE-GPLGIAGQG-PEG (SEQ ID NO:28) was 3,800 Da with the degree of polymerization of PEG n=48, which virtually coincides with the actual determination.

3. Gly-Pro-Gln-Gly-Ile-Trp-Gly-Gln-Gly (SEQ ID NO:18) Peptide (MMP Substrate)

3.1. Synthesis of 9-fluorenylmethyloxycarbonyl (Fmoc)-glycyl-prolyl-glutamyl-glycyl-isoleucyl -tryptophanyl-glycyl-glutamyl-glycine (Fmoc-Gly-Pro-Gln-Gly-Ile-Trp-Gly-Gln-Gly) (Fmoc-GPQGIWGQG: SEQ ID NO:29)

Fmoc removal was performed by adding 20% piperidine/dimethylformamide to Fmoc-Gly-Wang Resin. Dimethylformamide was added and the resin was washed. Then amino acids, 2-(1H-benzotriazol-1-yl)-1,1,3,3-tetramethyluronium hexafluorophosphate (HBTU), N,N-diisopropylethylamine (DIEA), and dimethylformamide were added to couple the amino acids to the amino acid residues bound to the resin. Dimethylformamide was added and the resin was washed. The procedure of removal of Fmoc, washing, coupling and washing was repeated until the amino acids of the entire sequence had been coupled. Then trifluoroacetic acid was added and stirred and the peptide was cut from the resin. The title compound was obtained by re-precipitating the peptide with ether and purifying the crude [product] that was obtained.

Confirmation of the product was performed by RP-HPLC analysis and MALDI-TOFMS analysis. When purity of the Fmoc-GPQGIWGQG (SEQ ID NO:29) was calculated from the peak surface area ratio as a result of RP-HPLC determination, purity of 98.4% was confirmed. Moreover, signals were observed at 1120 Da as a result of MALDI-TOFMS and the theoretical molecular weight was obtained, indicating that Fmoc-GPQGIWGQG (SEQ ID NO:29) had been synthesized.

3.2. Synthesis of 1 9-fluorenylmethyloxycarbonyl (Fmoc)-glycyl-prolyl-glutamyl-glycyl-isoleucyl -tryptophanyl-glycyl-glutamyl-glycine (Fmoc-Gly-Pro-Gln-Gly-Ile-Trp-Gly-Gln-Gly)-amidopropyl Polyoxyethylene Methyl Ether (Fmoc-GPQGIWGQG-PEG; SEQ ID NO:30)

Fifty milligrams of Fmoc-GPQGIWGQG (SEQ ID NO:29) were dissolved by adding 5 ml of N,N-dimethyl-formamide, 9.1 mg of N-hydroxysuccinimide were added, 29.5 mg of dicyclohexylcarbodiimide were further added, and the mixture was stirred for two hours at room temperature. Then a solution of 144 mg of methoxypolyethylene glycol-propylamine (SUNBRITE MEPA-20H, NOF Corporation) dissolved in 2.3 ml of N,N-dimethylformamide were added and reacted for 18 hours at 45° C. After the reaction, the reaction liquid was cooled to 0° C. or lower and filtered to remove the insoluble matter. Then it was rinsed with 5 ml of chloroform. This filtrate was passed through a strongly acidic cation exchange resin (DIAION SK-1, Mitsubishi Chemical Corporation) column and the unreacted methoxypolyethylene glycol-propylamine was removed. Then it was desiccated under reduced pressure in an evaporator. Twenty milliliters of ethyl acetate were added and the product was cooled to 0° C. or lower and filtered to obtain crude crystals. Five milliliters of water for injection were added to remove the impurities. Lyophilization was performed to obtain 70 mg of the title compound.

Progression of the reaction was monitored and the product was identified by thin-layer chromatography (TLC) using a silica gel plate. The substance was submitted to qualitative analysis by coloration with iodine vapor and comparison with the title substance using a mixed solvent of chloroform, methanol, and water at a mixture ratio (volume ratio) of 65:25:4. The end point of the reaction was confirmed based on shifting of the spots of methoxypolyethylene glycol-propylamine, which are detected near an Rf of 0.57, and of Fmoc-GPQGIWGQG-PEG (SEQ ID NO:30), which are detected near an Rf of 0.22, to spots detected near an Rf of 0.63 by the above-mentioned TLC.

3.3. Synthesis of H$_2$N-Gly-Pro-Gln-Gly-Ile-Trp-Gly-Gln-Gly-amidopropyl Polyoxyethylene Methyl Ether (GPQGIWGQG-PEG: SEQ ID NO:31)

First, 60 mg of the Fmoc-GPQGIWGQG-PEG (SEQ ID NO:30) obtained above were dissolved in 3 ml of N,N-dimethylformamide, 1 ml of piperidine was added, and a reaction was performed by stirring for 40 minutes at room temperature. The reaction liquid was desiccated under reduced pressure with an evaporator. Then 10 ml of ethyl acetate were added and the mixture was cooled to 0° C. or lower and filtered to obtain crude crystals. This purification process was repeated two more times to obtain 67 mg of the title compound. Progression of the reaction was monitored and the product was identified by the same TLC as described above. The reaction end point was confirmed based on shifting of the spot of Fmoc-GPQGIWGQG-PEG (SEQ ID NO:30), which is detected near an Rf of 0.62, to near an Rf of 0.21 and further, by ninhydrin coloration of the spot.

3.4. Synthesis of Distearoyl Phosphatidylethanolamine-glutaryl-Gly-Pro-Gln-Gly-Ile-Trp-Gly-Gln-Gly-amidopropyl Polyoxyethylene Methyl Ether (DSPE-GPQGIWGQG-PEG: SEQ ID NO:32)

First, 34 mg of the DSPE-Glt obtained above were dissolved in 0.3 ml of chloroform, and then 5.3 mg of N-hydroxysuccinimide and 16.5 mg of dicyclohexylcarbodiimide were added and stirred for two hours at room temperature. The reaction liquid was filtered to remove the insoluble matter and obtain distearoyl phosphatidylethanolamine glutaryl succinimide solution.

Twenty milligrams of the GPQGIWGQG-PEG (SEQ ID NO:31) obtained above were dissolved in 3 ml of chloroform, the distearoyl phosphatidylethanolamine glutaryl succinimide solution was added, and the mixture was stirred and reacted for five hours at 40° C. After the reaction, the product was filtered to remove the insoluble matter. Ten milliliters of ethyl acetate and 5 ml of hexane were added to this solution. After cooling, the mixture was filtered to obtain crude crystals. Purification was performed by repeating twice the crystallization process whereby 2 ml of ethyl acetate were added to the crude crystals and the mixture was cooled and filtered to obtain crystals. Five milligrams of the title compound were obtained.

Progression of the reaction was monitored and the product was identified by the same TLC as described above. Confirmation was based on the fact that the spot of GPQGI-WGQG-PEG (SEQ ID NO:31), which is detected near an Rf of 0.19, and the spot of DSPE-Glt, which is detected near an Rf of 0.23, had shifted to spots detected near an Rf of 0.46.

4. Gly-Hyp-Ala-Ser-Chg-Gln-Ser-Leu-Gly (SEQ ID NO:19) Peptide (PSA Substrate)

4.1. Synthesis of fluorenylmethyloxycarbonyl (Fmoc)-glycyl-hydroxyprolyl-alanyl-seryl -cyclohexylglycyl-glutamyl-seryl-isoleucyl-glycine (Fmoc-Gly-Hyp-Ala-Ser-Chg-Gln-Ser-Leu-Gly) (Fmoc-GHypASChgQSLG; SEQ ID NO:33)

Fmoc removal was performed by adding 20% piperidine/dimethylformamide to Fmoc-Gly-Wang Resin. Dimethylformamide was added and the resin was washed. Then amino acids, 2-(1H-benzotriazol-1-yl)-1,1,3,3-tetramethyluronium hexafluorophosphate (HBTU), N,N-diisopropylethylamine (DIEA), and dimethylformamide were added to couple the amino acids to the amino acid residues bound to the resin. Dimethylformamide was added and the resin was washed. The procedure of removal of Fmoc, washing, coupling and washing was repeated until the amino acids of the entire sequence had been coupled. Then trifluoroacetic acid was added and stirred and the peptide was cut from the resin. The title compound was obtained by re-precipitating the peptide with ether and purifying the crude [product] that was obtained.

Confirmation of the product was performed by RP-HPLC analysis and MALDI-TOFMS analysis. When purity of the Fmoc-GHypASChgQSLG (SEQ ID NO:33) was calculated from the peak surface area ratio as a result of RP-HPLC determination, purity of 100% was confirmed. Moreover, signals were observed at 1116 Da as a result of MALDI-TOFMS. The theoretical molecular weight was obtained, indicating that Fmoc-GHypASChgQSLG (SEQ ID NO:33) had been synthesized.

4.2. Synthesis of 9-fluorenylmethyloxycarbonyl (Fmoc)-glycyl-hydroxyprolyl-alanyl-seryl -cyclohexylglycyl-glutamyl-seryl-isoleucyl-glycine (Fmoc-Gly-Hyp-Ala-Ser-Chg-Gln-Ser-Leu-Gly) -amidopropyl polyoxyethylene methyl ether (Fmoc-GHypASChgQSLG-PEG; SEQ ID NO:34)

One-hundred milligrams of Fmoc-GHypASChgQSLG (SEQ ID NO:33) were dissolved by adding 5 ml of N,N-dimethylformamide, 17.8 mg of N-hydroxysuccinimide were added, 57.7 mg of dicyclohexylcarbodiimide were further added, and the mixture was stirred for two hours at room temperature. Then a solution of 280 mg of methoxypolyethylene glycol-propylamine (SUNBRITE MEPA-20H, NOF Corporation) dissolved in 2.3 ml of N,N-dimethylformamide were added and reacted for 18 hours at 45° C. After the reaction, the reaction liquid was cooled to 0° C. or lower and filtered to remove the insoluble matter. Then it was rinsed with 5 ml of chloroform. This filtrate was passed through a strongly acidic cation exchange resin (DIAION SK-1, Mitsubishi Chemical Corporation) column and the unreacted methoxypolyethylene glycol-propylamine was removed. Then it was desiccated under reduced pressure in an evaporator. Twenty milliliters of ethyl acetate were added and the product was cooled to 0° C. or lower and filtered to obtain crude crystals. Five milliliters of water for injection were added to remove the impurities. Lyophilization was performed to obtain 145 mg of the title compound.

Progression of the reaction was monitored and the product was identified by thin-layer chromatography (TLC) using a silica gel plate. The substance was submitted to qualitative analysis by coloration with iodine vapor and comparison with the title substance using a mixed solvent of chloroform, methanol, and water at a mixture ratio (volume ratio) of 65:25:4. The end point of the reaction was confirmed based on shifting of the spots of Fmoc-GHypASChgQSLG-PEG (SEQ ID NO:34), which are detected near an Rf of 0.15, to spots detected near an Rf of 0.55 by the above-mentioned TLC.

4.3. Synthesis of $H_2N$-Gly-Hyp-Ala-Ser-Chg-Gln-Ser-Leu-Gly-amidopropyl Polyoxyethylene Methyl Ether (GHypASChgQSLG-PEG: SEQ ID NO:35)

First, 140 mg of the Fmoc-GHypASChgQSLG-PEG (SEQ ID NO:34) obtained above were dissolved in 3 ml of N,N-dimethylformamide, 1 ml of piperidine was added, and a reaction was performed by stirring for 40 minutes at room temperature. The reaction liquid was desiccated under reduced pressure with an evaporator. Then 10 ml of ethyl acetate were added and the mixture was cooled to 0° C. or lower and filtered to obtain crude crystals. This purification process was repeated two more times to obtain 65 mg of the title compound. Progression of the reaction was monitored and the product was identified by the same TLC as described above. The reaction end point was confirmed based on shifting of the spot of Fmoc-GHypASChgQSLG-PEG (SEQ ID NO:34), which is detected near an Rf of 0.57, to near an Rf of 0.21 and further, by ninhydrin coloration of the spot.

4.4. Synthesis of Distearoyl Phosphatidylethanolamine-glutaryl-Gly-Hyp-Ala-Ser-Chg-Gln-Ser-Leu-Gly-amidopropyl polyoxyethylene methyl ether (DSPE-GHypASChgQSLG-PEG: SEQ ID NO:36)

First, 34 mg of the DSPE-Glt obtained above were dissolved in 0.3 ml of chloroform, and then 5.3 mg of N-hydroxysuccinimide and 16.5 mg of dicyclohexylcarbodiimide were added and stirred for two hours at room temperature. The reaction liquid was filtered to remove the insoluble matter and obtain distearoyl phosphatidylethanolamine glutaryl succinimide solution.

Milligrams of the GHypASChgQSLG-PEG (SEQ ID NO:35) obtained above were dissolved in 3 ml of chloroform, the distearoyl phosphatidylethanolamine glutaryl succinimide solution was added, and the mixture was stirred and reacted for five hours at 40° C. After the reaction, the product was filtered to remove the insoluble matter. Ten milliliters of ethyl acetate and 5 ml of hexane were added to this solution. After cooling, the mixture was filtered to obtain crude crystals. Purification was performed by repeating twice the crystallization process whereby 2 ml of ethyl acetate were added to the crude crystals and the mixture was cooled and filtered to obtain crystals. Fifty-eight milligrams of the title compound were obtained.

Progression of the reaction was monitored and the product was identified by the same TLC as described above. Confirmation was based on the fact that the spot of GHypASChgQSLG-PEG (SEQ ID NO:35), which is detected near an Rf of 0.17, and the spot of DSPE-Glt, which is detected near an Rf of 0.24, had shifted to spots detected near an Rf of 0.47. The product was confirmed by the presence of monomethoxyoxyethylene chains, peptide chains, and distearoyl phosphatidylethanol amine based on detection of the methyl group of the terminal end methoxy δ: near 3.4 ppm and the polyoxyethylene group δ: near 3.5 ppm derived from methoxypolyethylene glycol-propylamine, detection of δ: near 1.5 ppm derived from peptide, and further, detection of the terminal methyl group of the acyl group δ: near 0.9 ppm derived from distearoyl phosphatidylethanolamine by $^1$H-NMR.

5. DODASuc-peptide-PHEA Synthesis 5.1 Synthesis of β-benzyl-L-aspartic NCA

Five grams of β-benzyl-L-aspartate were added and suspended in 34 ml of tetrahydrofurane. Then 16 ml of a 20% phosgene-containing toluene solution were added to this solution and the solution was heated for 90 minutes at 60° C. under a nitrogen current to dissolve the β-benzyl-L-aspartic acid. This solution was poured into 140 ml of n-hexane and cooled to −20° C. and filtered to obtain 4.3 g of β-benzyl-L-aspartic NCA.

5.2 Synthesis of Polybenzyl-L-aspartic Acid (PBLA)

Three grams of β-benzyl-L-aspartic NCA were dissolved in 9 ml of dimethylformamide and 18.6 mg of methyl amine were dissolved in 0.3 ml of tetrahydrofurane. This solution was stirred for 18 hours at room temperature under a nitrogen current. This solution was poured into 150 ml of purified water and filtered to obtain 2 g of PBLA.

5.3 Synthesis of H$_2$N-glycyl-prolyl-glutamyl-glycyl-isoleucyl-alanyl-glycyl-tryptophanyl-glycine (Gly-Pro-Gln-Gly-Ile-Ala-Gly-Trp-Gly)-amidopolybenzyl-L-aspartate (GPQGIAGWG-PBLA; SEQ ID NO:37)

Forty-five milligrams of Fmoc-GPQGJAGWG (SEQ ID NO:21) were added and dissolved in 1 ml of N,N-dimethylformamide and then 156.6 mg of PyBOP (benzotriazol-1-yl-oxy-tri-pyrrolidino-phosphonium hexafluorophosphate) were added. Next, 46.1 mg of 1-hydroxybenzotriazole hydrate were dissolved in 0.6 ml of N,N-dimethylformamide and added to this solution and further, 50 μl of N-methyl morpholine were added to 0.5 ml of N,N-dimethyl formide. A solution of 70 mg of PBLA dissolved in 1 ml of N,N-dimethylformamide was added to this solution and reacted for 18 hours at room temperature under a nitrogen current. After the reaction, this solution was poured into 90 ml of ethyl ether and filtered to obtain Fmoc-GPQGIAGWG-PBLA (SEQ ID NO:38). The Fmoc-GPQGIAGWG-PBLA (SEQ ID NO:38) that was obtained was dissolved in 0.9 ml of N,N-dimethyl formamide, 0.3 ml of piperidine were added, and a reaction was performed by stirring for 30 minutes at room temperature. This solution was poured into 100 ml of ethyl ether and filtered to obtain GPQGIAGWG-PBLA (SEQ ID NO:37) crude crystals.

5.4 Synthesis Distearylamine-succinyl-Gly-Pro-Gln-Gly-Ile-Ala-Gly-Trp-Gly-amidopolyhydroxyethyl-L-aspartate (DODASuc-GPQGIAGWG-PHEA; SEQ ID NO:39)

Fifty milligrams of the GPQGIAGWG-PBLA (SEQ ID NO:37) obtained above were dissolved in 0.5 ml of chloroform and 9 μl of triethylamine were added. Five milligrams of N,N'-dicyclohexylcarbodiimide, 0.4 mg of 4-(dimethylamino)pyridinium-4-toluenesulfonate (J.S. Moore and S.I. Stupp, Macromolecules 23:65–70 (1990)), and 8.8 mg of N-succinyl-distearylamine (DODASuc, L. Schmitt, C. Dietrich, and R. Tampe in J. Am. Chem. Soc., 116:8485–8491(1994)) were dissolved in 1 ml of chloroform and added to this solution and reacted while stirring for 18 hours at room temperature. This solution was poured into 100 ml of methanol and filtered to obtain 40 mg of crude crystals. The crude crystals were dissolved in 0.1 ml of ethanol amine and 1.5 ml of N,N-dimethylformamide containing 11 mg of hydroxypyridine and reacted for 18 hours at 40° C. The crystallization process whereby crystals are obtained by pouring this solution into ethyl ether was repeated twice and purification by dialysis was performed to obtain 15 mg of the title compound.

When this sample was analyzed by MALDI-TOFMS, a signal derived from PEG was observed virtually in the middle at 4,961 Da. The calculated molecular weight of the DODASuc-GPQGIAGWG-PHEA (SEQ ID NO:39) was 4,906 Da with the degree of polymerization of the PHEA n=22 and virtually coincided with the actual determination.

5.5 Synthesis of H$_2$N-glycyl-prolyl-glutamyl-glycyl-isoleucyl-tryptophanyl-glycyl-glutamyl-glycine (Gly-Pro-Gln-Gly-Ile-Trp-Gly-Gln-Gly)-amidopolybenzyl-L-aspartate (GPQGIWGQG-PBLA; SEQ ID NO:40)

Forty-five milligrams of Fmoc-GPQGIWGQG (SEQ ID NO:29) were added and dissolved in 1 ml of N,N-dimethylformamide and 156.6 mg of PyBOP (benzotriazol-1-yl-oxy-tris-pyrrolidino-phosphonium hexafluorophosphate) were added. Then 46.1 mg of 1-hydroxybenzotriazole hydrate were dissolved in 0.6 ml of N,N-dimethylformamide and added to this solution and 50 μl of N-methyl morpholine and 0.5 ml of N,N-dimethylformamide were further added. A solution of 70 mg of PBLA dissolved in 1 ml of N,N-dimethylformide was added to this solution and reacted at room temperature for 18 hours under a nitrogen current. After the reaction, this solution was poured into 90 ml of ethyl ether and filtered to obtain Fmoc-GPQGIWGQG-PBLA (SEQ ID NO:41). The Fmoc-GPQGIWGQG-PBLA (SEQ ID NO:41) that was obtained was dissolved in 0.9 ml of N,N-dimethylformamide, 0.3 ml of piperidine were added, and a reaction was performed by stirring for 30 minutes at room temperature. This solution was poured into 100 ml of ethyl ether and filtered to obtain GPQGIWGQG-PBLA (SEQ ID NO:40) crude crystals.

5.6 Synthesis of Distearylamine-succinyl-Gly-Pro-Gln-Gly-Ile-Trp-Gly-Gln-Gly-amidopolyhydroxyethyl-L-aspartate (DODASuc-GPQGIWGQG-PHEA; SEQ ID NO:42)

Fifty milligrams of GPQGIWGQG-PBLA (SEQ ID NO:40) obtained above were dissolved in 0.5 ml of chloroform and 9 μl of triethylamine were added. Then 5 mg of N,N'-dicyclohexylcarbodiimide, 0.4 mg of 4-(dimethylamino)pyridinium-4-toluenesulfonate, and 8.8 mg of N-succinyl-distearylamine were dissolved in 1 ml of chloroform and added to this solution and reacted while being stirred for 18 hours at room temperature. This solution was poured into 100 ml of methanol and filtered to obtain 40 mg of crude crystals. The crude crystals were dissolved in 0.1 ml of ethanol amine and 1.5 ml of N,N-dimethylformamide containing 11 mg of hydroxypyridine and reacted for 18 hours at 40° C. After performing twice the crystallization process whereby this solution is poured into ethyl ether to obtain crystals, purification by dialysis was performed to obtain 5 mg of the title compound.

When this sample was analyzed by MALDI-TOFMS, a signal derived from PEG was observed virtually in the middle at 4,811 Da. The calculated molecular weight of the DODASuc-GPQGIWGQG-PHEA (SEQ ID NO:42) was 4,808 Da with the degree of polymerization of the PHEA n=21 and virtually coincided with the actual determination.

INDUSTRIAL APPLICABILITY

By means of the present invention, once a pharmaceutical preparation has reached the target diseased site, the water-soluble polymer is specifically cleaved from the pharmaceutical preparation at the target diseased site by using a lipid, substrate peptide of an enzyme that is secreted at the target diseased site, and a water-soluble polymer. Moreover, it is possible to realize drug delivery to target cells by altering the properties of the pharmaceutical preparation by separation of the water-soluble polymer from the pharmaceutical preparation.

In addition, the intermediates of the present invention are useful as intermediates for the direct production of conjugates (I), which are excellent for this tissue-specific delivery system.

The invention claimed is:

1. A conjugate comprising a lipid, a peptide, and a water-soluble polymer,
   wherein the lipid is conjugated to the amino terminus of the peptide by a peptide bond and the water-soluble polymer is conjugated to the carboxy terminus of the peptide by a peptide bond, wherein:
   the lipid is selected from the group consisting of phospholipids, fatty acids, glycolipids, ceramides, glycerides, and cholesterols;
   the peptide consists of a sequence selected from the group consisting of Gly-Pro-Gln-Gly-Ile-Ala-Gly-Trp-Gly (SEQ ID NO:22), Gly-Pro-Leu-Gly-Ile-Ala-Gly-Gln-Gly (SEQ ID NO:17), Gly-Pro-Gln-Gly-Ile-Trp-Gly-Gln-Gly (SEQ ID NO:18), and Gly-Hyp-Ala-Ser-Chg-Gln-Ser-Leu-Gly (SEQ ID NO:19), said peptide being a substrate for a secreted mammalian enzyme; and
   the water-soluble polymer is selected from the group consisting of polyethylene glycols, polyamino acids, polyhydroxyethylamino acids, and polyvinyl pyrrolidones.

2. The conjugate of claim 1, wherein the secreted mammalian enzyme is matrix metalloprotease-2 (MMP-2).

3. The conjugate of claim 1, wherein the secreted mammalian enzyme is prostate-specific antigen.

4. The conjugate according to claim 1, wherein the peptide is Gly-Pro-Gln-Gly-Ile-Ala-Gly-Trp-Gly (SEQ ID NO:22).

5. The conjugate according to claim 1, wherein the peptide is Gly-Pro-Leu-Gly-Ile-Ala-Gly-Gin-Gly (SEQ ID:17).

6. The conjugate according to claim 1, wherein B is Gly-Pro-Gln-Gly-Ile-Trp-Gly-Gln-Gly (SEQ ID:18).

7. The conjugate according to claim 1, wherein the peptide is Gly-Hyp-Ala-Ser-Chg-Gln-Ser-Leu-Gly (SEQ ID:19).

8. The conjugate according to claim 1, wherein the lipid is a phospholipid.

9. The conjugate according to claim 1, wherein the water-saluble polymer is a polyethylene glycol.

10. The conjugate of claim 1, wherein the lipid is substituted with a carboxylic anhydride.

11. The conjugate of claim 1, wherein the lipid has an activated carboxyl group.

12. The conjugate of claim 1, wherein one end of the water-soluble polymer is substituted with one or more methoxy groups.

13. The conjugate of claim 1, wherein one end of the water-soluble polymer is substituted with an amino group.

* * * * *